US011656228B2

(12) United States Patent
Sarver, Jr. et al.

(10) Patent No.: US 11,656,228 B2
(45) Date of Patent: *May 23, 2023

(54) COMPOSITIONS FOR USE IN MYCOTOXIN EXTRACTION

(71) Applicant: Neogen Corporation, Lansing, MI (US)

(72) Inventors: Ronald W. Sarver, Jr., Dexter, MI (US); Ronald D. Beaubien, Jr., Jackson, MI (US); Nanduri Viswaprakash, Dewitt, MI (US)

(73) Assignee: NEOGEN CORPORATION, Lansing, MI (US)

( * ) Notice: Subject to any disclaimer, the term of this patent is extended or adjusted under 35 U.S.C. 154(b) by 422 days.

This patent is subject to a terminal disclaimer.

(21) Appl. No.: 16/779,974

(22) Filed: Feb. 3, 2020

(65) Prior Publication Data

US 2020/0191786 A1    Jun. 18, 2020

Related U.S. Application Data

(60) Division of application No. 15/639,287, filed on Jun. 30, 2017, now Pat. No. 10,598,661, which is a continuation of application No. 15/171,244, filed on Jun. 2, 2016, now abandoned, which is a continuation of application No. PCT/US2014/060018, filed on Oct. 10, 2014.

(51) Int. Cl.
  G01N 33/569    (2006.01)
  A23L 5/20      (2016.01)
  A23L 11/30     (2016.01)

(52) U.S. Cl.
  CPC .......... *G01N 33/56961* (2013.01); *A23L 5/23* (2016.08); *A23L 5/27* (2016.08); *A23L 5/273* (2016.08); *A23L 11/32* (2016.08); *A23L 11/34* (2016.08); *A23V 2002/00* (2013.01); *G01N 2333/37* (2013.01); *G01N 2469/10* (2013.01)

(58) Field of Classification Search
  CPC ............ A23L 11/32; A23L 11/34; A23L 5/23; A23L 5/27; A23L 5/273; A23V 2002/00; G01N 2333/37; G01N 2469/10; G01N 33/56961
  See application file for complete search history.

(56) References Cited

U.S. PATENT DOCUMENTS

| | | |
|---|---|---|
| 2011/0014319 A1 | 1/2011 | Davis |
| 2011/0070328 A1 | 3/2011 | Tangni |

FOREIGN PATENT DOCUMENTS

| | | |
|---|---|---|
| AU | 2014200349 A1 | 2/2014 |
| CN | 102836694 | 12/2012 |
| DE | 19821509 A1 | 11/1999 |
| WO | 2011008276 A2 | 1/2011 |
| WO | 2013116847 A1 | 8/2013 |

OTHER PUBLICATIONS

Amadasi, Alessio, et al. "Explaining cyclodextrin-mycotoxin interactions using a "natural" force field" Bioorganic & Medicinal Chemistry, vol. 15, Issue 13, Jul. 1, 2007, pp. 4585-4594.
Appell, M. et al. "Effects of Cyclodextrins and Surfactants On the Fluorescence Detection of Mycotoxins." 38th Great Lakes Regional Meeting of the American Chemical Society. May 13, 2009.
Brewster, et al. Use of 2-Hydroxypropyl-B-cyclodextrin as a Solubilizing and Stabilizing Excipient for Protein Drugs, Pharm. Research, 1991, vol. 8, issue 6, pp. 792-795.
Dall'Asta, C. et al. "Complexation of the mycotoxin zearalenone with B-cyclodextrin: Study of the interaction and first promising applications." Mycotoxin Research vol. 24, No. 1, Mar. 14-18, 2008.
Dall'Asta, C. et al. "Complexation of zearalenone and zearalenols with native and modified ß-cyclodextrins." J Incl Phenom Macrocycl Chem, 64:331-340, Mar. 25, 2009.
Dall'Asta, Chiara, et al. Fluoresence Enhancement of Aflatoxins Using Native and Substituted Cyclodextrins. Journal of Inclusion Phenimena and Macrocyclic Chemistry 45: 257-263, 2003.
Galaverna, et al. "Cyclodextrins as selectors for mycotoxin recognition," 2008, World Mycotoxin Journal, vol. 1, No. 4, pp. 397-406; Published Online: Aug. 19, 2008.
Hashemi, Javad, et al. "Enhanced spectrofluorimetric determination of aflatoxin B1 in wheat by second-order standard addition method" Talanta, vol. 75, Issue 4, May 30, 2008, pp. 1075-1081.
International Search Report and Written Opinion of corresponding PCT Application No. PCT/US2014/060018 dated Jun. 8, 2015.
Kruger, M. "Untersuchungen zum Einschluss von Mykotoxinen" University of Applied Sciences Bachelor Thesis, Mar. 9, 2009.
Maragos, C. et al. "Use of cyclodextrins as modifiers of fluorescence in the detection of mycotoxins." Food Additives and Contaminants, 25(2): 164-171, Feb. 2008.
Maragos, Chris M., et al. "Capillary electrophoresis of the mycotoxin zearalenone using cyclodextrin-enhanced fluorescense" Journal of Chromatography A, vol. 1143, Issues 1-2, Mar. 2, 2007, pp. 252-257.
Reid, et al. "Nonexhaustive Cyclodextrin-Based Extraction Technique for the Evaluation of PAH Bioavailability," Environ. Sci. Technol., 2000, vol. 34, No. 15, pp. 3174-3179.
Srivastava, et al. Annexure: Buffers, Solutions and Miscellaneous. Procedures, Protocols in Semen Biology (Comparing Assays), Springer Nature Singapore Pte Ltd., 2017, pp. 285-288.
Third Party Observations submitted May 29, 2019 in EP Application No. 20140795702, 7 pages.
Third Party Observations submitted Nov. 24, 2016 in correspondence PCT Application No. PCT/US2014/060018.
Third Party Observations submitted Oct. 5, 2020 in US2020-0191786, 4 pages.

(Continued)

*Primary Examiner* — Galina M. Yakovleva
(74) *Attorney, Agent, or Firm* — Honigman LLP; Douglas H. Siegel; Jonathan P. O'Brien

(57) ABSTRACT

The present invention relates to aqueous compositions comprising cyclodextrins or carbohydrates. The present invention also relates to the use of such compositions in the binding and removal of mycotoxins from foodstuff. The invention also includes compositions that show a broad affinity for mycotoxins.

8 Claims, 11 Drawing Sheets

(56) References Cited

OTHER PUBLICATIONS

Valle-Algarra, F.M., et al. "Detection and Analysis by Classical Techniques" Encyclopedia of Food Microbiology (Second Edition), 2014, pp. 862-868.
Zhou, Youxiang, et al. "A study of florescence properties of citrinin in ß-cyclodextrin aqueous solution and different solvents" Journal of Luminescence, vol. 132, Issue 6, Jun. 2012, pp. 1437-1445.
Wikipedia page for Phosphate-buffered saline on Jun. 19, 2019 in U.S. Appl. No. 15/639,287.
Mbundi, Lubinda, et al. Advances in the Analysis of Challenging Food Contaminants: Nanoparticles, Bisphenols, Mycotoxins, and Brominated Flame Retardants. Advance in Molecular Toxicology, vol. 8, pp. 35-105 (2014).
Taherimaslak, Zohreh, et al. Magnetically assisted solid phase extraction using Fe3O4 nanoparticles combined with enhanced spectrofluorimetric detection for aflatoxin M1 determination in milk samples. Analytics Chimica Acta 842 (2014) 63-69.
Bennett, J.W., et al. Mycotoxins. Clinical Microbiology Reviews, vol. 16, No. 3, Jul. 2003, pp. 497-516.
J. Horsky, J. Pitha, Hydroxypropyl Cyclodextrins Potential Synergism with Carcinogens, J. Pharm. Science, 85(1), 96-100, 1996.†
M. Appell, et al., Synthesis and evaluation of cyclodextrin based polymers for patulin extraction from aqueous solutions, J. Inclusion Phenomena and Macrocyclic Chemistry, 68(1-2), 117-122, 2010.†
P. Cozzini, et al., Mycotoxin Detection Plays 'Cops and Robbers': Cyclodextrin Chemosensors as Specialized Police?, Int. J. Molecular Sci., 2008, 9, 2474-2494.†
M. Appell, C.M. Maragos, A Closer Look at Cyclodextrins in Mycotoxin Analysis—in Mycotoxin Prevention and Control in Agriculture, ACS Symposium Series vol. 1031, Chapter 20, 293-305, 2009.†
R. Verrone, et al., Effect of B-cyclodextrin on spectroscopic properties of ochratoxin A in aqueous solution, J. Incl. Phenom. Macrocyclic Chem., 57, 475-479, 2007.†
Joao Augusto, Development of a Screening Method for Determination of Aflatoxins, Master of Science Thesis, The University of Georgia, U.S.A., 2004.†
S. Uchiyama, et al., Protein-Binding of Ochratoxin A and Its Extractability from Proteinous Food, J. Food Hyg. Soc. Japan (Shokuhin Eiseigaku Zasshi), 26.6, 651-657, 1985.†

† cited by third party

Fig 1: Structure of Aflatoxin B₁ and related aflatoxins.

Ochratoxin A

Ochratoxin B

Ochratoxin C

COMPOSITIONS FOR USE IN MYCOTOXIN EXTRACTION

CROSS-REFERENCE TO RELATED APPLICATIONS

This application is a divisional of U.S. application Ser. No. 15/639,287, filed Jun. 30, 2017, which is a continuation of U.S. application Ser. No. 15/171,244, filed Jun. 2, 2016, now abandoned, which is a continuation of PCT Application No. PCT/US2014/060018, filed Oct. 10, 2014, which is incorporated herein by reference in its entirety.

FIELD OF THE INVENTION

The present invention relates to aqueous compositions comprising cyclodextrins or carbohydrates. The present invention also relates to the use of such compositions in the binding and removal of mycotoxins from foodstuff. The invention also includes compositions that show a broad affinity for mycotoxins.

BACKGROUND OF THE INVENTION

Aflatoxins are mycotoxins produced by mold, such as *Aspergillus flavus* and are found in many forms of human foods, such as cereals, grains, and peanut products. Different forms of aflatoxin, including aflatoxin B1, B2, G1, and G2 are known for their toxicity and carcinogenicity. Various studies suggested a link of aflatoxin exposure with an increased occurrence of liver and lung cancer. Aflatoxin B1 (AFB1), the most toxic compound in this series, has been found to be one of the most potent carcinogens occurring naturally and it was classified as Group I human carcinogen by the International Agency for Research on Cancer (IARC) in 1987. Accordingly, the presence of aflatoxins in food has been recognized as a threat to human health. The presence of these mycotoxins in various foods can be caused by direct contamination via grains and grain products or by the presence of mycotoxins and their metabolites in animal tissues, milk and meat caused by animal consumption of contaminated feed. There exist a great number of reports that suggest intoxication of humans by the consumption of aflatoxins contaminated agricultural products. Epidemiological studies have shown that aflatoxins exposure is associated with increased risk of hepatocellular carcinoma, particularly in combination with hepatitis B virus. Also, it has been shown that the potency of aflatoxins increases in individuals with liver conditions such as hepatitis B infection.

Due to their frequent occurrence and their severe toxicity, guidelines and tolerance levels of aflatoxins have been set in several countries. Wheat is susceptible to these fungi infections through its growth, harvest, transport and storage. Iran has set a maximum residue limit of 5 $\mu g K g^{-1}$ for AFB1 in wheat for imports. Accordingly, the low tolerance for food contamination by aflatoxins causes serious economic losses.

Improvement in the determination of mycotoxin levels in grains has been an ongoing effort, and current methods include TLC, fluorescence polarization assay, HPLC, radioimmunoassay (RIA), ELISA, and fiber optic based immunoassays. These methods have some drawbacks, for example chromatographic methods require extended cleanup steps and derivatization after extraction in order to get rid of interfering substances, commercially available ELISAs require enzymatic reactions and washing and separation of bound and free label.

The use of spectrofluorimetry analysis is also hampered when testing natural samples such as blood, urine, foods, cereals, grains, and peanut products. The procedure is made difficult by the complexity of matrices which show a great variety of natural fluorescent compounds whose spectra often overlap the analyte signal. This situation therefore demands tedious separation steps to enable determination of the analyte.

With respect to removing the mycotoxins from the grain, current extraction methods for the removal of mycotoxins from foodstuffs, such as grains, predominantly involve the use of organic based liquid compositions, such as methanol/water mixtures and the like. Herein, compositions and methods are presented for the aqueous based extraction and recovery of mycotoxins from foodstuffs. The compositions also show broad affinity for mycotoxins, and therefore remove a wide variety of toxic contaminants simultaneously.

SUMMARY OF THE INVENTION

The invention described herein relates to compositions and methods related to the extraction of and quantification of mycotoxins from foodstuff. In some embodiments, the compositions used herein are aqueous compositions and do not comprise an organic solvent. Accordingly, a benefit of some aspects of the present invention is the extraction of mycotoxins from foodstuff using a fully aqueous solution. Another benefit of the present invention is that the compositions described herein extract a broad range of mycotoxins.

In one aspect, the invention includes an aqueous composition comprising a cyclodextrin, polyol, non-foaming surfactant, or a carbohydrate. In some embodiments of this aspect, the aqueous composition is a fully aqueous composition.

In some embodiments, the cyclodextrin is an alpha, beta, or gamma cyclodextrin of formula I $$\left[ \begin{array}{c} OR \\ RO \\ OR \end{array} O \right]_n \quad I$$

wherein
n is 6, 7, or 8;
each R is independently hydrogen or a substituent having the formula A $$\text{---} E \text{---} OH; \quad A$$

wherein each E is independently selected from $C_{1-8}$ aliphatic, $C_{1-8}$ cycloaliphatic, and $C_{1-8}$ heterocycloaliphatic, or combinations thereof; and an exemplary sample of the cyclodextrin of formula I possesses, on average, 0-10 formula A substituents per cyclodextrin molecule, and wherein the hydroxyl substituent of each formula A may independently be further substituted by another formula A substituent.

In one aspect, the invention includes a method of extracting one or more mycotoxins from foodstuffs, comprising contacting said foodstuffs with any composition described herein.

In one aspect, the invention includes a pack or kit comprising
a. a composition described herein;
b. a lateral flow detection apparatus comprising a test strip and mycotoxin detector; and
c. instructions for extracting mycotoxins from a sample of foodstuff with said composition, and subsequently contacting the lateral flow detection apparatus with said composition.

DETAILED DESCRIPTION OF THE INVENTION

Definitions

Figure 1:
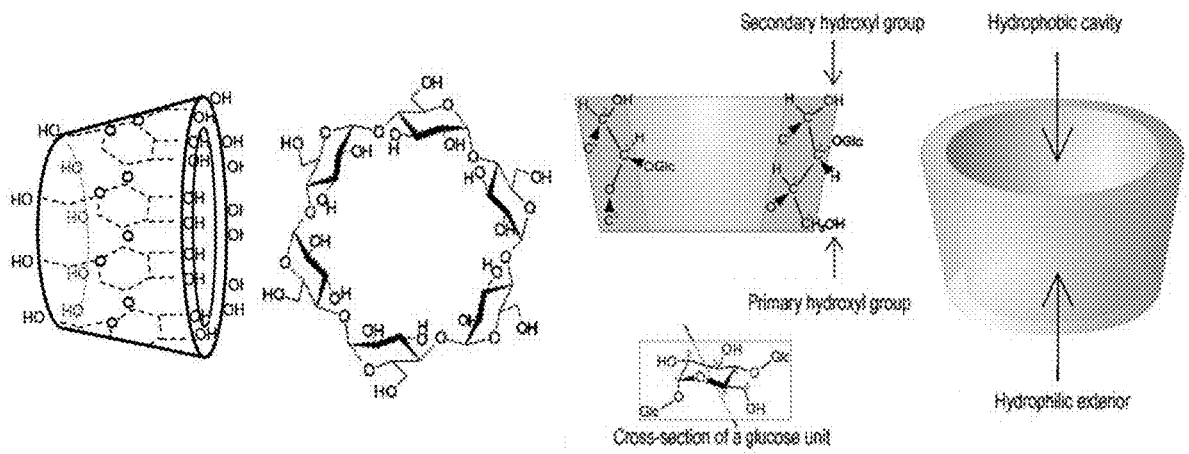
FIG. 1 is a depiction of α-cyclodextrin from various perspectives.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkyl carbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic) alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched.

Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, aryl aminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, a "carbocycle" or "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycle" or "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic) carbonylamino, (aryl)carbonylamino, (araliphatic)carbonylamino, (heterocycloaliphatic)carbonylamino, ((heterocycloaliphatic) aliphatic)carbonylamino, (heteroaryl)

carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic)aliphatic)carbonyl, (aralipathic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

As used herein, the term "mycotoxin" means any toxic metabolite, for example metabolites produced by organisms of the fungi kingdom. Without limitation, the term "mycotoxin" can refer to the toxic chemical products produced by fungi that readily colonize crops. Without limitation, examples of mycotoxins include aflatoxin, ochratoxin, fumonisin, zearalenone, deoxynivalenol (DON), T2 toxin, and ergot toxin.

As used herein, the term "foodstuff" means any substance suitable for consumption as food by an organism, for example foodstuff for consumption by animals or humans. Specific examples of animals are a 'companion animal' or livestock.

As used herein, the term "MQ water" means type 1 water according to the standards of ASTM (American Society for Testing and Materials).

As used herein, the term "fully aqueous composition" describes a composition that comprises water, but does not comprise an organic solvent, for example, a buffer that does not include any organic solvent.

As used herein, the term "non-detect" [grain] means a sample of foodstuff, for example grain, that is known to contain a non-detectable amount of mycotoxin. Non-detect sample are used in the experiments and examples disclosed herein to establish a baseline signal in the various tests, such as REVEAL® Q+(a lateral flow assay) and VERATOX® (an enzyme linked immunoassay).

As used herein, the term "cyclodextrin" is synonymous with the term "cycloamylose," and describes a family of compounds made up of sugar molecules bound together in a ring (cyclic oligosaccharides). The term "α-cyclodextrin" indicates that the cyclodextrin has 6 sugar moieties in its cyclic structure, the term "β-cyclodextrin" indicates that the cyclodextrin has 7 sugar moieties in its cyclic structure, and the term "γ-cyclodextrin" indicates that the cyclodextrin has 8 sugar moieties in its cyclic structure.

As used herein, the term "surfactant" means a compound comprising a hydrophobic region, for example a branched, linear, cyclic, or aromatic hydrocarbon, and a hydrophilic region, for example an anionic, cationic, zwitterionic, or other moiety capable of forming hydrogen bonds with water. A "non-foaming surfactant" is a special type of surfactant that resists forming a foam when used for the intended application.

As used herein, the term "buffer" describes a solution that resists changes in pH when acid or alkali is added to it. Examples of simple buffering agents used in aqueous buffers are citric acid, acetic acid, sodium or potassium dihydrogen phosphate ($NaH_2PO_4$ or $KH_2PO_4$), disodium or dipotassium hydrogen phosphate ($Na_2HPO_4$ or $K_2HPO_4$), CHES (N-Cyclohexyl-2-aminoethanesulfonic acid), and boronic acid (borate). Examples of other common buffering agents are TAPS (3-{[tris(hydroxymethyl)methyl]amino}propanesulfonic acid), Bicine (N,N-bis(2-hydroxyethyl)glycine), Tris (tris(hydroxymethyl)methylamine), Tricine (N-tris(hydroxymethyl)methylglycine), TAPSO (3-[N-Tris(hydroxymethyl)methylamino]-2-hydroxypropanesulfonic Acid), HEPES (4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), Cacodylate (dimethylarsinic acid), SSC (saline sodium citrate), IVIES (2-(N-morpholino)ethanesulfonic acid), and Succinic acid (2(R)-2-(methylamino)succinic acid).

CAVASOL® W7 HP is standard grade hydroxypropyl-beta-cyclodextrin, produced by Wacker Chemie AG, and is a low cost highly soluble beta-cyclodextrin derivative. The product data for CAVASOL® W7 HP are provided in the table below.

| PRODUCT DATA | | |
| --- | --- | --- |
| Specification data | Inspection Method | Value |
| Molar substitution (per anhydro glucose unit) | NMR | 0.6-0.9 |
| unsubstituted cyclodextrin | HPLC | max. 1.0% |
| Residue on ignition | USP | max. 2.5% |
| Propylene glycols | GC | max. 5.0% |
| Loss of drying | halogen dryer | max. 7.0% |
| Typical general characteristics | Inspection method | Value |
| Solubility in water at 24° C. | | 2300 g/l |

EMBODIMENTS

In one aspect, the invention includes an aqueous composition comprising a cyclodextrin, polyol, non-foaming surfactant, or a carbohydrate. In some embodiments of this aspect, the aqueous composition is a fully aqueous composition.

In one embodiment of this aspect, the aqueous composition comprises a carbohydrate. In another embodiment, the carbohydrate is selected from starch, glycogen, cellulose, chitin, and sucrose. In a further embodiment, the carbohydrate is sucrose. In another further embodiment, the carbohydrate is cellulose.

In one embodiment of this aspect, the aqueous composition comprises a polyol. In another embodiment, the polyol is selected from maltitol, sorbitol, xylitol, erythritol, and isomalt. In a further embodiment, the polyol is sorbitol. In still a further embodiment, the polyol is D-sorbitol.

In one embodiment of this aspect, the aqueous composition comprises a non-foaming surfactant. In another embodiment, the non-foaming surfactant is selected from Butylpolyalkylene oxide block copolymer, alkyl ethoxylate, Tridecyl alcohol ethoxylate, Nonylphenol ethoxylate, Octylphenol ethoxylate, Tristyrylphenol ethoxylate, Decylalcohol ethoxylate, Alkylphenol alkoxylate, Alcohol ethoxylate, Alcohol ethoxylate, Ethoxylate phosphate ester, α-(4-Nonylphenyl)-ω-hydroxy-poly(oxy-1,2-ethanediyl), Fatty acid ethoxylate, and TRITON™ CF-32 (an ethoxylate). In further embodiment, the α-(4-Nonylphenyl)-ω-hydroxy-poly(oxy-1,2-ethanediyl) is branched.

In another embodiment, the non-foaming surfactant is selected from TOXIMUL® 8320 (a butyl polyalkylene oxide block copolymer); ECOSURF® EH3 (an alcohol ethoxylate); MAKON® TD18, MAKON® 10, MAKON® OP-9, MAKON® TSP-40, MAKON® DA4, and MAKON® N-1-10 (nonylphenol ethoxylates); BIO-SOFT® EC600 and BIO-SOFT® N1-3 (linear alcohol (c11) ethoxylates); STEPFAC™ 8170 (a nonylphenol poe-10 phosphate ester); TERGITOL™ (a secondary alcohol ethoxylate), NINEX® MT-630F (an ethoxylated derivative of fatty acid); and TRITON™ CF-32. In a further embodiment, the non-foaming surfactant is selected from TOXIMUL® 8320, ECOSURF® EH3, and NINEX® MT-630F. In a further embodiment, the non-foaming surfactant is selected from TOXIMUL® 8320, ECOSURF® EH3, and NINEX® MT-630F. In another further embodiment, the non-foaming surfactant is selected from Butylpolyalkylene oxide block copolymer, alkyl ethoxylate, and Fatty acid ethoxylate.

In still another embodiment, the Butylpolyalkylene oxide block copolymer is TOXIMUL® 8320, the alkyl ethoxylate is ECOSURF® EH3, the Tridecyl alcohol ethoxylate is MAKON® TD18, the Nonylphenol ethoxylate is MAKON® 10, the Octylphenol ethoxylate is MAKON® OP-9, the Tristyrylphenol is ethoxylate MAKON® TSP-40, the Decylalcohol ethoxylate is MAKON® DA4, the Alkylphenol alkoxylate is MAKON® N-1-10, the Alcohol ethoxylate is BIO-SOFT® EC600, the Alcohol ethoxylate is BIO-SOFT® N1-3, the Ethoxylate phosphate ester is STEPFAC™ 8170, the α-(4-Nonylphenyl)-ω-hydroxy-poly(oxy-1,2-ethanediyl) is TERGITOL™, and the Fattyacid ethoxylate is NINEX® MT-630F. In further embodiment, the α-(4-Nonylphenyl)-ω-hydroxy-poly(oxy-1,2-ethanediyl) is branched.

In another embodiment of this aspect, the aqueous composition comprises a cyclodextrin. In one embodiment, the aqueous composition further comprises a buffer. In a further embodiment, the buffer is a phosphate buffer.

In another embodiment, the aqueous composition comprises:
a. 1-15 g/L of sodium chloride (NaCl);
b. 5-20 g/L of disodium phosphate ($Na_2HPO_4$);
c. 0.1-2.0 g/L of sodium dihydrogen phosphate ($NaH_2PO_4$); and
d. 10-150 g/L of a cyclodextrin.

In still another embodiment, the cyclodextrin is an alpha, beta, or gamma cyclodextrin of formula I

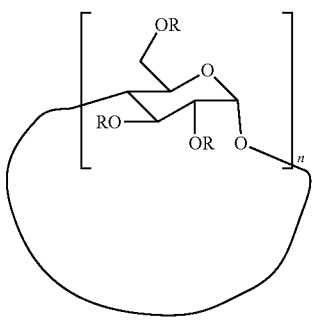

wherein
n is 6, 7, or 8;
each R is independently hydrogen or a substituent having the formula A

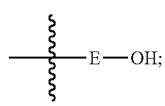

wherein each E is independently selected from $C_{1-8}$ aliphatic, $C_{1-8}$ cycloaliphatic, and $C_{1-8}$ heterocycloaliphatic, or combinations thereof; and an exemplary sample of the cyclodextrin of formula I possesses, on average, 0-10 formula A substituents per cyclodextrin molecule, and wherein the hydroxyl substituent of each formula A may independently be further substituted by another formula A substituent.

In some embodiments, n is 7.

In one embodiment, an exemplary sample of the cyclodextrin of formula I possesses, on average, 3-6 substituents of formula A per cyclodextrin molecule. In a further embodiment, an exemplary sample of the cyclodextrin of formula I possesses, on average, 4.1-5.1 substituents of formula A per cyclodextrin molecule.

In another embodiment, each E is $C_{1-8}$ alkyl. In a further embodiment, each E is independently selected from methylene, ethylene, n-propylene, isopropylene, n-butylene, 1,1-dimethylethylene, 1,2-dimethylethylene,

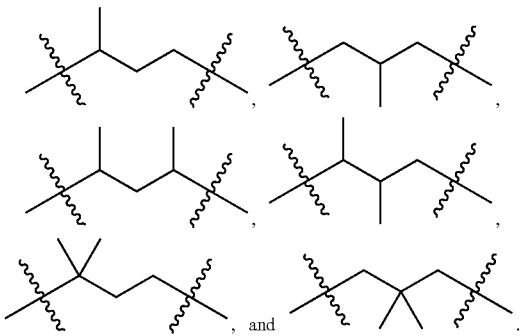

In still a further embodiment, each E is isopropylene.
In another embodiment, the substituent having the formula A is

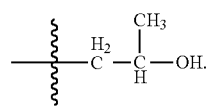

In another embodiment, the cyclodextrin is a standard grade hydroxypropyl-beta-cyclodextrin.

In some embodiments, the sodium chloride is present in an amount of 6-10 g/L. In a further embodiment, the sodium chloride is present in an amount of about 8 g/L. In some embodiments, the disodium phosphate is present in an amount of 10-16 g/L. In a further embodiment, the disodium phosphate is present in an amount of about 13.8 g/L. In some embodiments, the sodium dihydrogen phosphate is present in an amount of 0.35-0.70 g/L. In a further embodiment, the sodium dihydrogen phosphate is present in an amount of about 0.51 g/L. In some embodiments, the cyclodextrin is present in an amount of 20-40 g/L. In a further embodiment, the cyclodextrin is present in an amount of about 30 g/L. In some embodiments, the cyclodextrin is present in an amount of 110-130 g/L. In a further embodiment, the cyclodextrin is present in an amount of about 120 g/L.

In one embodiment of this aspect, the aqueous composition comprises:
a. about 8 g/L of sodium chloride (NaCl);
b. about 13.8 g/L of disodium phosphate ($Na_2HPO_4$);

c. about 0.51 g/L of sodium dihydrogen phosphate ($NaH_2PO_4$); and
d. about 30 g/L of a standard grade hydroxypropyl-beta-cyclodextrin.

In a further embodiment, the aqueous composition consists essentially of:
a. water;
b. about 8 g/L of sodium chloride (NaCl);
c. about 13.8 g/L of disodium phosphate ($Na_2HPO_4$);
d. about 0.51 g/L of sodium dihydrogen phosphate ($NaH_2PO_4$); and
e. about 30 g/L of a standard grade hydroxypropyl-beta-cyclodextrin.

In another embodiment of this aspect, the aqueous composition comprises:
a. about 8 g/L of sodium chloride (NaCl);
b. about 13.8 g/L of disodium phosphate ($Na_2HPO_4$);
c. about 0.51 g/L of sodium dihydrogen phosphate ($NaH_2PO_4$); and
d. about 120 g/L of a standard grade hydroxypropyl-beta-cyclodextrin.

In a further embodiment, the aqueous composition consists essentially of:
a. water;
b. about 8 g/L of sodium chloride (NaCl);
c. about 13.8 g/L of disodium phosphate ($Na_2HPO_4$);
d. about 0.51 g/L of sodium dihydrogen phosphate ($NaH_2PO_4$); and
e. about 120 g/L of a standard grade hydroxypropyl-beta-cyclodextrin.

In one aspect, the invention includes a method of extracting one or more mycotoxins from foodstuffs, comprising contacting said foodstuffs with any composition described herein.

In one embodiment of this aspect, the foodstuff is a grain. In another embodiment, the grain is selected from barley, corn, fonio, kamut, millet, oats, popcorn, rice, rye, sorghum, spelt, teff, triticale, wheat, dry distiller grain, and corn gluten meal. In a further embodiment, the grain is selected from corn, barley, wheat, and rice.

In another embodiment of this aspect, the mycotoxin is selected from aflatoxin, ochratoxin, fumonisin, zearalenone, deoxynivalenol, T2 toxin, and ergot toxin. In a further embodiment, the mycotoxin is selected from fumonisin, aflatoxin, zearalenone, and ochratoxin.

In another embodiment, the method comprises the steps of:
a) contacting the foodstuff with the composition;
b) optionally, removing the composition from the foodstuff; and
c) contacting a lateral flow detection apparatus comprising a test strip and mycotoxin detector with the composition from step b.

In one aspect, the invention includes a pack or kit comprising
a. a composition described herein;
b. a lateral flow detection apparatus comprising a test strip and mycotoxin detector; and
c. instructions for extracting mycotoxins from a sample of foodstuff with said composition, and subsequently contacting the lateral flow detection apparatus with said composition.

EXAMPLES

In order that the invention described herein may be more fully understood, the following examples are set forth. It should be understood that these examples are for illustrative purposes only and are not to be construed as limiting this invention in any manner.

Materials and Methods

Lateral Flow Devices

Without limitation, lateral flow immunochromatographic devices comprise a membrane, often nitrocellulose, with a capture line deposited on the membrane. The capture line may be an antibody with avidity to the analyte, such as a mycotoxin, or the capture line may be an analyte bound to the membrane. In the latter case, the analyte is often conjugated to a protein to improve adhesion to the membrane. Laminar flow devices that have an antibody capture line(s), will bind analyte at the capture line. Bound analyte is often detected by a second antibody (the label) that is conjugated to nanoparticle gold, latex, or other visualizing agent. This format is often referred to as a direct assay format since assay response increases directly with analyte concentration. Laminar flow devices that have analyte at the capture line(s), detect the analyte using a labeled antibody that can be part of the device. For these devices, when analyte is present in the sample, the analyte competes with the label and the response decreases, which is referred to as an indirect assay format.

In addition to the basic construction, laminar flow devices may also incorporate sample pads to aid in wicking sample onto the membrane and conjugate pads that have labeled antibody bound to them for use with analyte detection. Devices may also contain absorbant pads at the end of the device to aid in flow of the sample on the lateral flow device. Laminar flow devices made by Neogen, such as REVEAL® and REVEAL® Q+(quantitative) have been used to detect mycotoxins extracted with the aqueous based extractants. Other laminar flow and ELISA devices from Charm Sciences Inc., Romer Labs, R-Biopharm, and Envirologix may also be used to detect myctotoxins extracted using the aqueous based extractants.

REVEAL® Q+

REVEAL® Q+ devices are single-step lateral flow immunochromatographic assays based on a competitive immunoassay format intended for the quantitative testing of specific mycotoxins, such as DON, aflatoxins, fumonisin, ochratoxin, T-2/HT-2, and zearalenone, in a foodstuff sample.

VERATOX® ELISA

VERATOX® is a competitive direct ELISA (Enzyme-Linked Immunesorbent Assay) that provides a quantitative analysis of specific mycotoxins, such as DON, aflatoxins, fumonisin, ochratoxin, T-2/HT-2, and zearalenone, in a foodstuff sample.

Buffers

It is to be understood that the compositions of the present invention can be prepared using a broad range of buffers. Acceptable buffers to be used with the present invention include, but are not limited to buffers made with buffering agents selected from citric acid, acetic acid, sodium or potassium dihydrogen phosphate ($NaH_2PO_4$ or $KH_2PO_4$), disodium or dipotassium hydrogen phosphate ($Na_2HPO_4$ or $K_2HPO_4$), CHES (N-Cyclohexyl-2-aminoethanesulfonic acid), boronic acid (borate), TAPS (3-{[tris(hydroxymethyl)methyl]amino}propanesulfonic acid), Bicine (N,N-bis(2-hydroxyethyl)glycine), Tris (tris(hydroxymethyl)methylamine), Tricine (N-tris(hydroxymethyl)methylglycine), TAPSO (3-[N-Tris(hydroxymethyl)methylamino]-2-hydroxypropanesulfonic Acid), HEPES (4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'- bis(2-ethanesulfonic acid)), Cacodylate (dimethylarsinic acid), SSC (saline sodium citrate), IVIES (2-(N-morpholino)ethanesulfonic acid), and Succinic acid (2(R)-2-(methylamino)succinic acid).

General Procedures

Grain samples are ground using a mill such that 95% of the sample will pass through a 20-mesh sieve as specified by the U.S. Department of Agriculture Grain Inspection, Packers and Stockyards Administration (GIPSA) test performance specifications for quantitative test kits. Extractant powder or liquid extractant is then added to the dry ground grain sample. Sample size is typically between 10 grams and 50 grams, the latter is specified by GIPSA. The amount of liquid extractant added would typically be 30 mL to 50 mL for 10 gram samples and 150 mL to 250 mL for 50 gram samples. In cases where the extractant is a powder, between 1 gram and 6 grams of powder is added for 10 gram samples and between 5 grams and 30 grams of powder is added for 50 gram samples. Then distilled water is added at the volumes indicated for liquid extractant. Extractant and grain samples are shaken for 3 min (10 gram samples) or blended for 30 seconds (50 gram samples). The extract is filtered using a syring filter packed with glass wool or through a membrane filter, such as Whatmann filter paper. The extract can then be assayed for mycotoxins using various methods such as laminar flow, ELISA, other immunoassays, or various analytical methods including spectroscopic and mass spectrometer based assays.

Experimental Procedure

Water soluble chemicals were evaluated for their ability to extract mycotoxins from corn and wheat samples containing known amounts of mycotoxin. Mycotoxins extracted included aflatoxin, fumonisin, zearalenone, deoxynivalenol (DON) and ochratoxin. Chemicals evaluated as possible mycotoxin extractants were selected for evaluation based on physical properties including mycotoxin affinity and the ability to promote dissociation of mycotoxins or other interfering components from grain matrices. A variety of surfactants, proteins, lipids, carbohydrates, glycerols, and buffers were initially evaluated using existing REVEAL® Q+ quantitative lateral flow devices. These evaluations included extraction of reference materials containing mycotoxin near the maximum residue limit (MRL). In addition, grains confirmed to be free of detectable mycotoxin were extracted. Extractants that showed sufficient differentiation in response for MRL samples versus non-detect grain were further evaluated by extracting several levels of mycotoxins to determine the concentration response curve. A small robustness study was also performed for hydroxypropyl β-cyclodextrin (CAVASOL®) extraction of aflatoxin and DON.

Preliminary Evaluation of Chemicals for Aflatoxin Recovery from Ground Corn

Initial screening involved extraction of aflatoxin from ground corn using chemicals in water or solutions prepared using Neogen PBS (phosphate buffered saline, pH 7.4) packets. Table 1 lists the results obtained for the chemicals that showed some differentiation between ground corn reference material containing 21 ppb aflatoxin and non-detect ground corn. Although the extractions were not optimized in this preliminary screening evaluation, an indication of aflatoxin recovery was provided by examining the ratio of REVEAL® Q+ results for the 21 ppb reference material compared to non-detect corn samples also referred to as signal to noise (S/N). These results indicated gelatin, Stabilzyme Select, cyclodextrin, glycerol, lecithin and non-foaming surfactants were able to recover aflatoxin from ground corn. Stabilzyme contains albumin which has been shown to bind mycotoxins. Further evaluation was necessary to determine how well the materials could recover aflatoxin from ground corn containing several levels of aflatoxin and whether the materials could extract other mycotoxins from ground corn and wheat.

Cyclodextrins for Mycotoxin Extraction

Cyclodextrins are cyclical carbohydrates that form a cavity capable of sequestering portions of other molecules and improving their aqueous solubilities. This property has been utilized to help solubilize poorly soluble drugs. Cylodextrins have also been shown to enhance the fluorescence of zearalenone. FIG. 1 shows the structure of α-cyclodextrin and includes depictions of the hydrophobic cavity that binds other molecules. The size of the cavity increases with the number of carbohydrates in the ring system. The primary and secondary alcohols can be substituted with various functional groups to alter the hydrophobicity of the cavity and hydrophilicity of the cyclodextrin exterior. This can be useful in tailoring the binding affinity of the cyclodextrin for other molecules. Table 1 lists REVEAL® Q+ for Aflatoxin results for several cyclodextrins. β-cylcodextrin and the substituted β-analogs evaluated provided better recoveries of aflatoxin from ground corn than γ-cyclodextrin. Although heptakis (2-6-di-O-methyl)-β-cyclodextrin provided the best signal to noise in the preliminary evaluation, low cost raw material is also an important consideration. Standard grade material was not available for heptakis-β-cyclodextrin but was available for β-cyclodextrin (Cavamax) and 2-hydroxypropyl-β-cyclodetrin (CAVASOL®). The latter two raw materials were further evaluated for recoveries of other mycotoxins.

TABLE 1

Extraction Results for Aflatoxin Reference Material Corn Using REVEAL ® Q+ Aflatoxin Lateral Flow Devices

| Extractant (1% solution in Neogen PBS unless stated otherwise) | Q+ Result for 21 ppb Aflatoxin MRM (10 g/30 mL Neogen PBS, N = 2) | Q+ Result for Non-Detect Aflatoxin MRM (10 g/30 mL) | Ratio of Results for 21 ppb/ND (S/N) | Aflatoxin Extract Dilution Factor |
| --- | --- | --- | --- | --- |
| Glycerol, 5% in water | 12.5 | 4.6 | 2.7 | 3.5 |
| Glycerol ethoxylate, 5% in water | 16.1 | 8.1 | 2.0 | 3.5 |
| β-cyclodextrin in water | 14.9 | 4.5 | 3.3 | 3.5 |
| Heptakis (2,6-di-O-methyl)-β-cyclodextrin in water | 33.0 | 8.7 | 3.8 | 3.5 |

TABLE 1-continued

Extraction Results for Aflatoxin Reference Material Corn Using REVEAL® Q+ Aflatoxin Lateral Flow Devices

| Extractant (1% solution in Neogen PBS unless stated otherwise) | Q+ Result for 21 ppb Aflatoxin MRM (10 g/30 mL Neogen PBS, N = 2) | Q+ Result for Non-Detect Aflatoxin MRM (10 g/30 mL) | Ratio of Results for 21 ppb/ND (S/N) | Aflatoxin Extract Dilution Factor |
|---|---|---|---|---|
| (2-hydroxypropyl)-β-cyclodextrin in water | 23.3 | 9.1 | 2.6 | 3.5 |
| γ-cyclodextrin in water | 20.0 | 9.9 | 2.0 | 3.5 |
| Stabilzyme Select, 6% in water | 9.4 | 4.5 | 2.1 | 6 |
| Stabilzyme Select, 3% in water | 13.8 | 5.5 | 2.5 | 3.5 |
| Porcine Gelatin, 1.5% in water | 6.2 | 1.5 | 4.1 | 3.5 |
| Eugenol, 1% in water/0.1 M NaOH | 11.4 | 7.7 | 1.5 | 6 |
| Thymol, 2% in water/7% etoh | 8.0 | 4.4 | 1.8 | 6 |
| TOXIMUL ® 8320 | 20.5 | 5.1 | 4.0 | 2 |
| ECOSURF ® EH3, 0.0125% | 21.8 | 5.2 | 4.2 | 2 |
| MAKON ® TD18 | 23.4 | 9.8 | 2.4 | 2 |
| MAKON ® 10 | 31.8 | 9 | 3.5 | 2 |
| TRITON ® CF-32 | 24.6 | 6.3 | 3.9 | 2 |
| Dissolvine GL47S | 24.6 | 7.9 | 3.1 | 2 |
| Betaine | 19.5 | 12.8 | 1.5 | 2 |
| Soy Lecithin | 20.7 | 10.4 | 2.0 | 2 |
| ECOSURF ® EH6 | 22.9 | 12.9 | 1.8 | 2 |
| MAKON ® TSP40 | 21.3 | 9.3 | 2.3 | 2 |
| BIO-SOFT ® N1-3 | 22.5 | 6.8 | 3.3 | 2 |
| BIO-SOFT ® EC600 | 23.5 | 7.3 | 3.2 | 2 |
| MAKON ® DA-4 | 20.4 | 8.8 | 2.3 | 2 |
| MAKON ® OP-9 | 26.8 | 5.3 | 5.1 | 2 |
| STEPFAC ™ 8170-U | 27.5 | 10.7 | 2.6 | 2 |

Non-Foaming Surfactants

Ethoxylate surfactants have repeating ethoxy functionality similar to ethanol. Since ethanol is a good extractant for several mycotoxins the repeating ethoxy functionality could prove useful for aqueous based mycotoxin extraction. Table 2 below lists several commercially available ethoxylate surfactants and other non-foaming surfactants that were evaluated. These surfactants were chosen from an array of surfactants to span a range of moles of ethoxylate (moles EO) and hydrophilic, lipophilic balance (HLB). Moles of ethoxylate and HLB alter aqueous solubility and polarity of the solution which can alter extraction properties. Tables 3A and 3B list REVEAL® Q+ for Aflatoxin results for the non-foaming surfactants that were able to extract aflatoxin and other mycotoxins from reference materials. Each entry provides the REVEAL® Q+ results for extraction of the mycotoxin at a level near the MRL and a non-detect sample. In addition the signal to noise and extract dilution factor are listed. Of these surfactants, TOXIMUL® and ECOSURF® EH3 provided good recoveries of zearalenone, aflatoxin, fumonisin and ochratoxin from ground corn and aflatoxin from dry distillers grain (DDG). NINEX® MT-630F also had a good profile of mycotoxin recoveries.

TABLE 2

Physical properties of several commercially available non-foaming ethoxylate surfactants and other non-foaming surfactants that are evaluated herein

| Supplier | Trade name | Chemical Class | HLB | Moles EO | Physical State |
|---|---|---|---|---|---|
| Stepan | MAKON ® N1-10 | Alkylphenol alkoxylate | | | solid |
| | BIO-SOFT ® EC600 | Alcohol ethoxylate | 12.2 | 7 | liquid |
| | BIO-SOFT ® N1-3 | Alcohol ethoxylate | 8.7 | 3 | liquid |
| | MAKON ® DA4 | Decylalcohol ethoxylate | 10 | 4 | liquid |
| | STEPFAC ™ 8170 | Ethoxylate phosphate ester | | 8 | liquid |
| | Ninex MT-630F | Fattyacid ethoxylate | 16 | | wax |
| | MAKON ® 10 | Nonylphenol ethoxylate | 13 | 10 | liquid |
| | MAKON ® OP-9 | Octylphenol ethoxylate | 13.5 | 9 | liquid |
| | MAKON ® TD-18 | Tridecyl alcohol ethoxylate | 16 | 18 | solid |
| | MAKON ® TSP-40 | Tristylphenol ethoxylate | 16 | 40 | solid |
| | TOXIMUL ® 8320 | Butylpolyalkylene oxide block copolymer | 12 | | |
| Dow | TERGITOL ™ | Nonionic | 12.1 | | Liquid |
| | ECOSURF ® EH-3 | Ethoxylate | | | Liquid |

TABLE 3A

Additional REVEAL ® Q+ Results Using Non-Foaming Surfactants to Extract Ground Corn Reference Materials Containing Other Mycotoxins

| Name (1% sol except specified) | Zen-Corn (100 mM PBS pH 8) | Afla-Corn (1:1 DF) (NeoPBS) | Afla-DDG (10.8% EtOH Final in Dil) (100 mM PBS pH 8) (6 min inc, acidic extract) |
|---|---|---|---|
| TOXIMUL ® 8320 | 194 ppb = 241.1 ND = 40.7 (S:N 5.20) (1:10df) | 21 ppb = 20.5 ND = 5.1 (S:N 4.0) | 21 ppb = 8.1 ND = 1.6 (S:N 5.06) |
| ECOSURF ® EH3 (0.0125%) | 194 ppb = 171.7 ND = 32.9 (S:N 5.20) (1:2.5 df) | 21 ppb = 21.76 ND = 5.22 (S:N 4.17) | 21 ppb = 7.0 ND = 4.4 (S:N 1.59) |
| MAKON ® TD18 | Not Tested | 21 ppb = 23.4 ND = 9.8 (S:N 2.39) | 21 ppb = 9.6 ND = 2.1 (S:N 4.57) |
| MAKON ® 10 | Not Tested | 21 ppb = 31.8 ND = 9.0 (S:N 3.53) | 21 ppb = 6.3 ND = 0.9 (S:N 7.00) |
| NINEX ® MT-630F (0.5%) | 194 ppb = 252.6 ND = 42.9 (S:N 5.9) (1:7 df) | Not Tested | 18.7 ppb = 7.2 ND = 3.5 (S:N 2.057) |

TABLE 3B

Additional REVEAL ® Q+ Results Using Non-Foaming Surfactants to Extract Ground Corn Reference Materials Containing Other Mycotoxins

| Name (1% sol except specified) | Afla-DDG (10.8% EtOH Final in Dil) (100 mM PBS pH 8) (6 min inc, neutral extract) | Fum-Corn (100 mM PBS pH 8) | Ochra-Corn 43.7 ppb extract pre-diluted with ND extract to achieve ~20 ppb. (35% MeOH) |
|---|---|---|---|
| TOXIMUL ® 8320 | 21 ppb = 10.2 ND = 2.6 (S:N 3.92) | 4.3 ppm = 4.0 ND = 0.1 (S:N 40) (1:3 DF) | 43.7 ppb = 26.3 ND = 1.7 (S:N 15.5) (1:4 DF) |
| ECOSURF ® EH3 (0.0125%) | 21 ppb = 12.2 ND = 3.6 (S:N 3.39) | 4.3 ppm = 3.9 ND = 0.0 (S:N >39) (1:2 DF) | 43.7 ppb = 16 ND = 1.7 (S:N 9.4) (1:2 DF) |
| MAKON ® TD18 | 21 ppb = 15.0 ND = 4.5 (S:N 3.33) | Not Tested | 43.7 ppb = 17.8 ND = 1.9 (S:N 9.4) (1:2 DF) |
| MAKON® 10 | 21 ppb = 3.4 ND = 4.1 (S:N 0.83) | Not Tested | 43.7 ppb = 22.4 ND = 1.4 (S:N 16) (1:4 DF) |
| NINEX ®MT-630F (0.5%) | Not Tested | Not Tested | "20" ppb = 24.5 ND = 3.1 (S:N 7.9) (1:2 DF) |

Figure 2A:
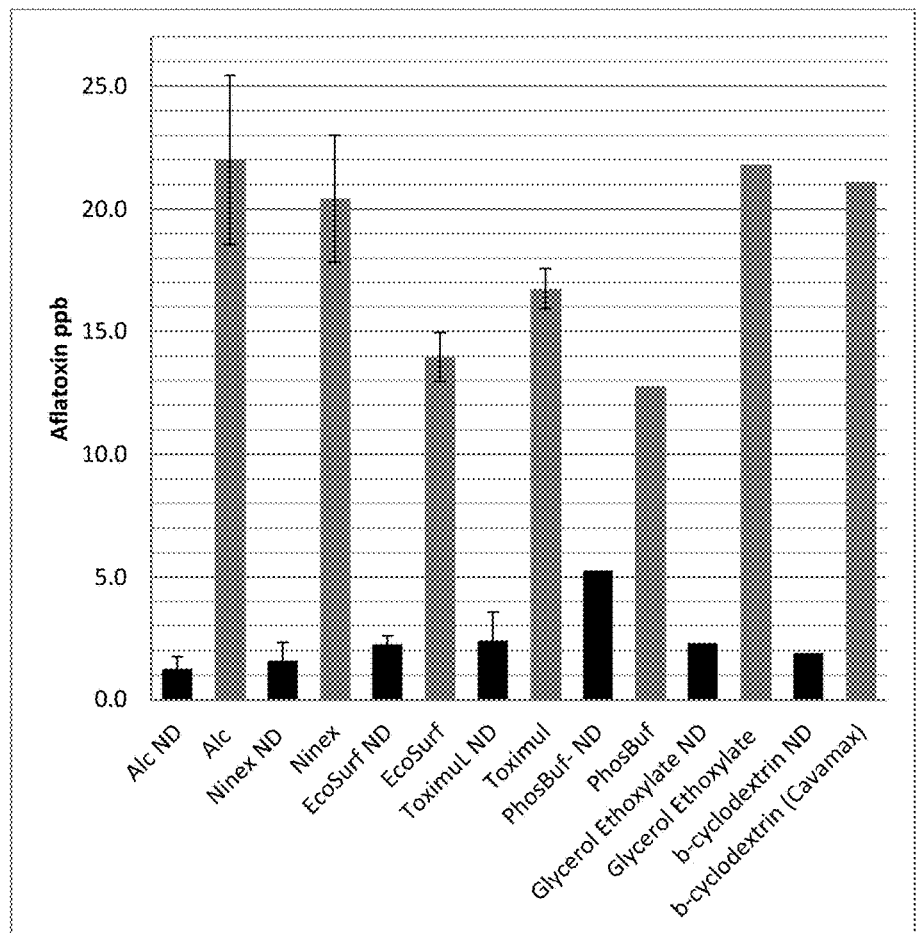
FIG. 2A is a bar graph showing REVEAL® Q+ for aflatoxin results for ground corn reference material containing 19 ppb total aflatoxin or non-detect ground corn.

REVEAL® Q+ Evaluations of the Most Promising Aflatoxin Extractants for Extraction of Other Mycotoxins Reveal® Q+ for Aflatoxin AccuScan III results are shown in FIG. 2A for the most promising surfactants and cylcodextrins identified form the preceding studies. Black bars are results obtained for non-detect ground corn and gray bars are results obtained for ground corn reference material containing 19 ppb total aflatoxin. These initial screening results were obtained using the ASIII calibration curve-set parameters supplied with the kit. The first set of bars are the results obtained using the current 65% ethanol based extraction diluted 1:6 into diluent. The next 3 sets of bars are extraction results for Ninex, EcoSurf and Toximul surfactants at 1% in water with the filtered extract diluted into kit diluent that also contained ethanol. The final ethanol concentration in the diluted filtrate was 10.8% which matched the ethanol amount for extracts that used the 65% ethanol solvent extraction process after it was diluted 1:6 in diluent. That is followed by extraction results for phosphate buffer and finally extraction results for 1% glycerol ethoxylate and 1% β-cyclodextrin in water diluted into kit diluent plus ethanol. Again, the final concentration of ethanol was 10.8%. The closest results to the ethanol extraction were obtained with Ninex, glycerol ethoxylate and β-cyclodextrin.

Figure 2B:
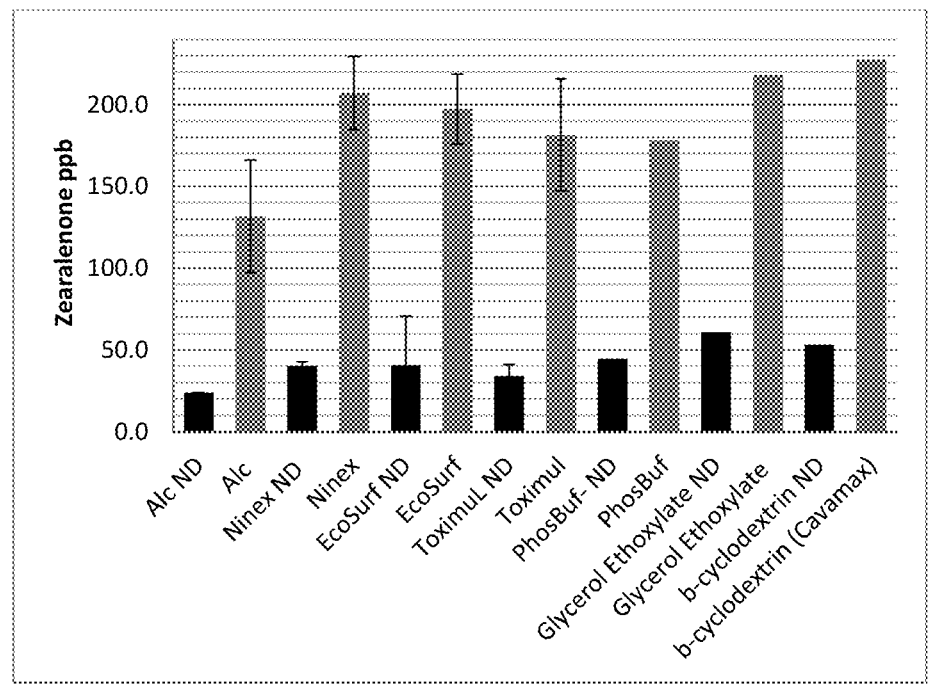
FIG. 2B is a bar graph showing REVEAL® Q+ for zearalenone results for ground corn reference material containing 194 ppb total zearalenone or non-detect ground corn.

REVEAL® Q+ for Zearalenone AccuScan III results are shown in FIG. 2B for ground corn reference material containing 194 ppb zearalenone or non-detect ground corn. Black bars are results obtained for non-detect ground corn and gray bars are results obtained for ground corn reference material containing 194 ppb zearalenone. These initial screening results were obtained using the ASIII calibration curve-set parameters supplied with the kit. All the extractants provided good recovery of zearalenone. Although the amount of zearalenone was elevated for the non-detect samples, those results were based on the existing solvent based calibration curve. The non-detect bias would be corrected with a curve set established using the aqueous based extractant.

Figure 2C:
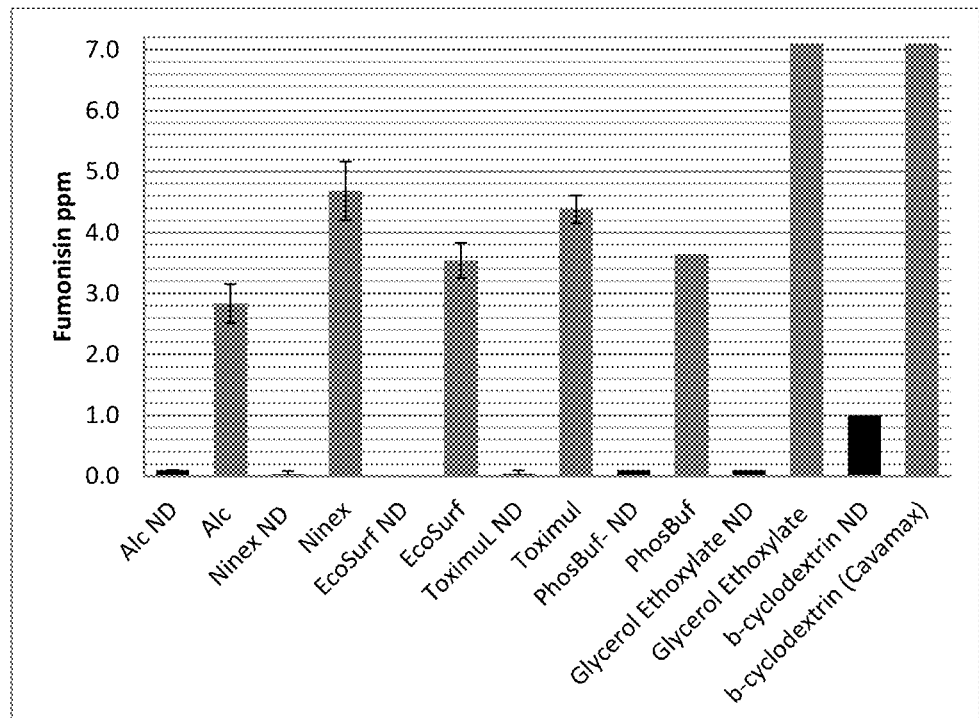
FIG. 2C is a bar graph showing REVEAL® Q+ for fumonisin results for ground corn reference material containing 5 ppm fumonisin or non-detect ground corn.

REVEAL® Q+ for Fumonisin AccuScan III results are shown in FIG. 2C for ground corn reference material containing 5 ppm total fumonisin or non-detect ground corn. Black bars are results obtained for non-detect ground corn and gray bars are results obtained for ground corn reference material containing 5 ppm total fumonisin. These initial screening results were obtained using the ASIII calibration curve-set parameters supplied with the kit. Non-detect samples were within specification even with the existing solvent based calibration curve. All the extractants shown in FIG. 2C provided good recoveries of total fumonisin, but results were elevated for glycerol ethoxylate and β-cyclodextrin compared to HPLC determined levels. Establishing a calibration curve with the latter extractants would be expected to correct the bias from the solvent based calibration.

Figure 2D:
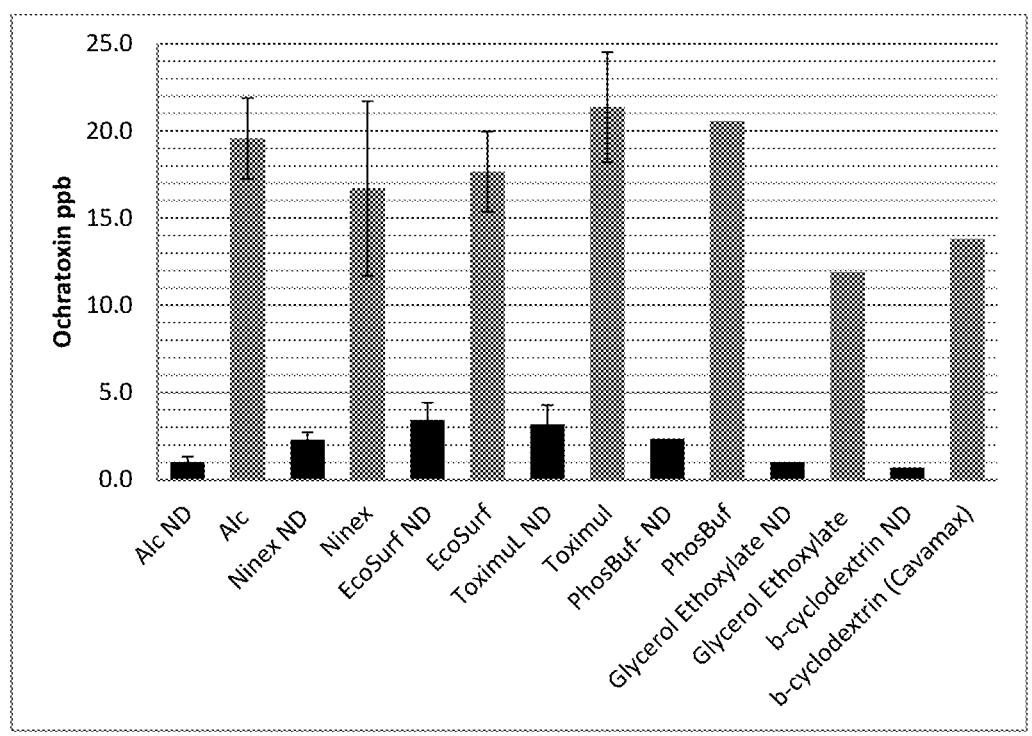
FIG. 2D is a bar graph showing REVEAL® Q+ for ochratoxin results for ground corn reference material containing 20 ppb ochratoxin or non-detect ground corn.
Figure 3A:
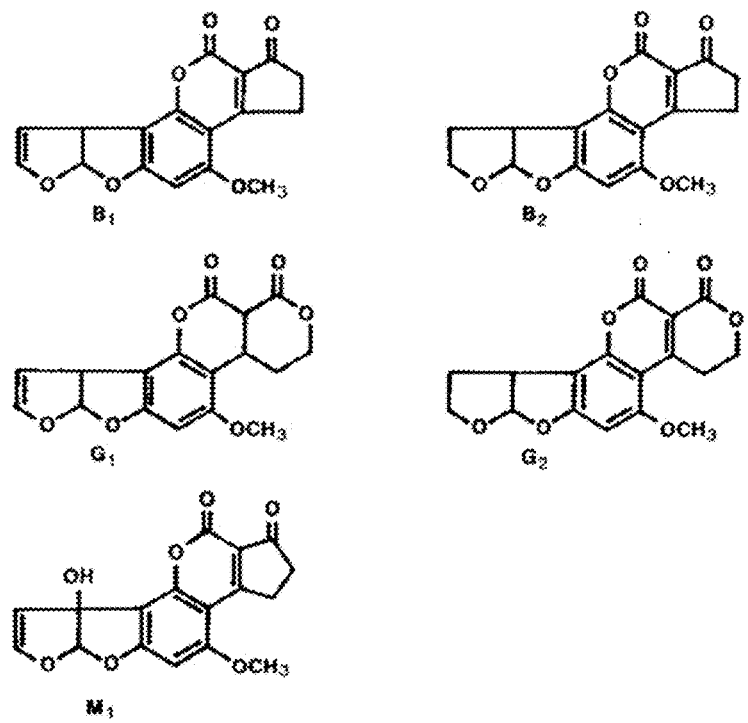
FIG. 3A is a pictorial representation of the structure of aflatoxin analogs.
Figure 3B:
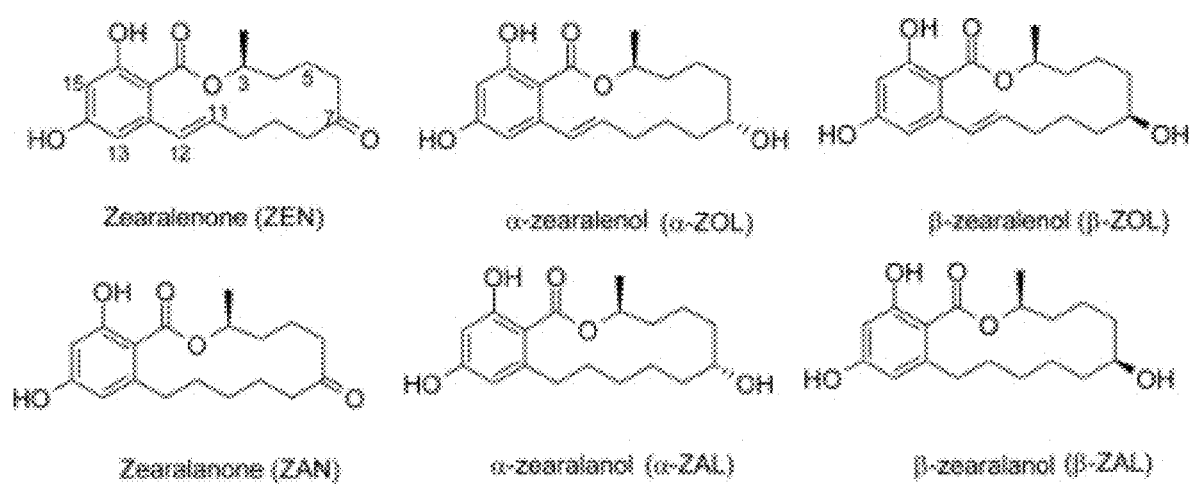
FIG. 3B is a pictorial representation of the structure of zearalenone analogs.
Figure 3C:
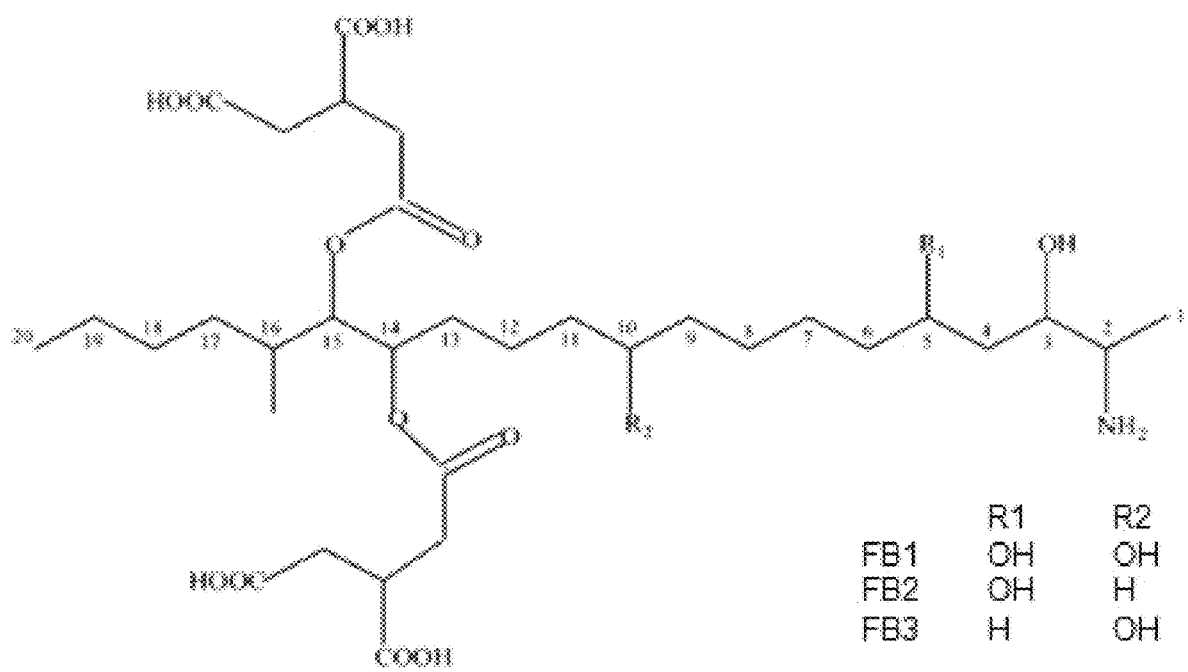
FIG. 3C is a pictorial representation of the structure of fumonisin analogs.
Figure 3D:
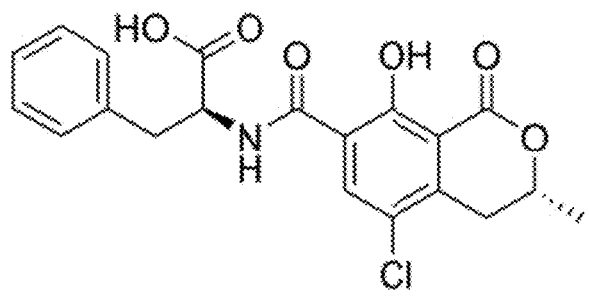
FIG. 3D is a pictorial representation of the structure of ochratoxin analogs.
Figure 3D:
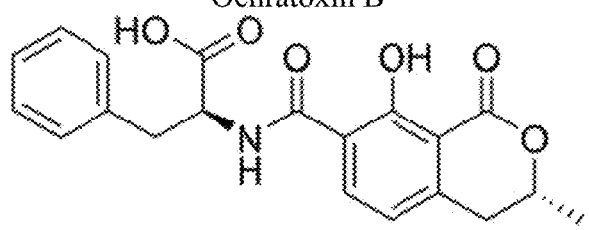
Figure 3D:
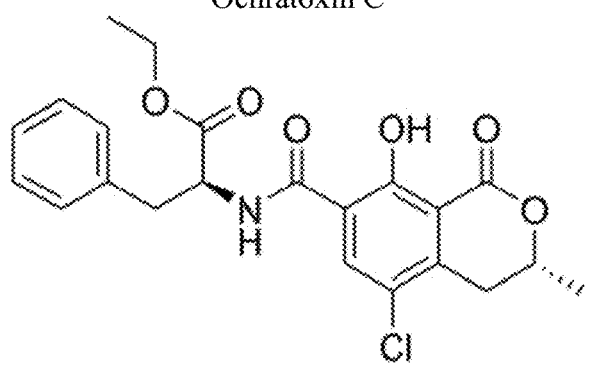
Figure 3E:
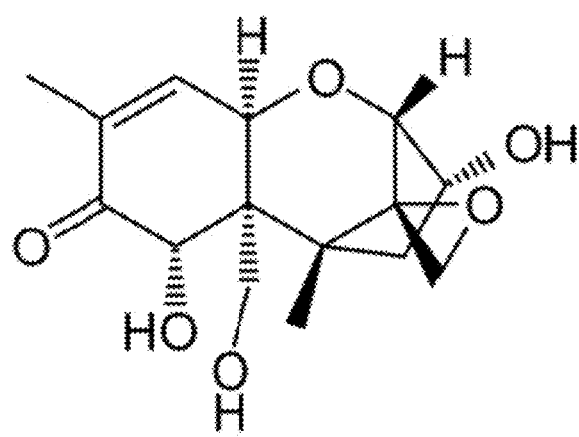
FIG. 3E is a pictorial representation of the structure of deoxynivalenol (DON)/vomitoxin.

REVEAL® Q+ for Ochratoxin AccuScan III results are shown in FIG. 2D for ground corn reference material containing 20 ppb Ochratoxin or non-detect ground corn. Black bars are results obtained for non-detect ground corn and gray bars are results obtained for ground corn reference material containing 20 ppb Ochratoxin. These initial screening results were obtained using the ASIII calibration curve-set parameters supplied with the kit. All the extractions were diluted into kit diluent containing 23% methanol. Methanol was needed in the diluent for the current lateral flow devices to keep the non-detect levels within specification using the existing solvent based calibration curve. The surfactants provided good recoveries of ochratoxin, while the results for glycerol ethoxylate and b-cyclodextrin were low but based on the supplied solvent based calibration.

Results for phosphate buffer, pH 8.0 plus 137 mM sodium chloride were included in FIG. 2 based on results obtained for fumonisin and ochratoxin. FIGS. 3A-E shows the structures for the mycotoxins involved in these studies. Fumonisin and ochratoxin contain carboxylic acids capable of forming salts at basic pH. Salts of weak acids are known to improve aqueous solubilities. Phosphate/NaCl buffer pH 8.0 provided respectable recoveries of the mycotoxins including fumonisin and ochratoxin. Phosphate/NaCl buffer, pH 8 was then used as the base formulation to which the other promising extractants, ethoxylate surfactants and cyclodextrins, were added for evaluation of mycotoxin recoveries.

Figure 4:
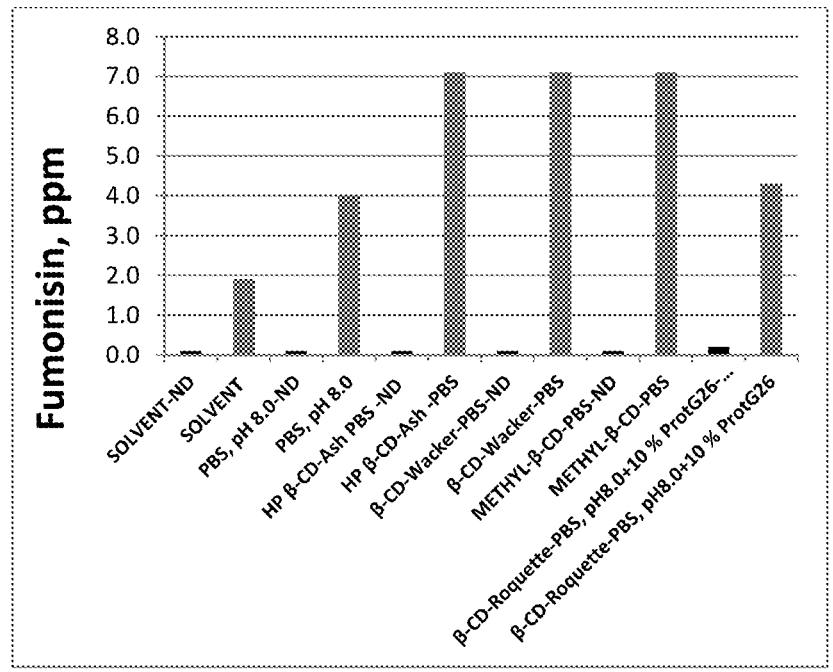
FIG. 4 is a bar graph showing REVEAL® Q+ for fumonisin results for extractions of ground corn reference material using different cylcodextrins in phosphate buffered saline, ph 8.0.

FIG. 4 shows the results obtained for fumonisin extractions from ground corn reference materials using several different cyclodextrins in PBS, pH 8.0 as the extractant. These initial screening results were obtained using the ASIII calibration curve-set parameters supplied with the kit and extracts diluted into Q+ fumonisin diluent. Although the recoveries were greater than expected for the cyclodextrins the dilution could be adjusted to align the results to expected or a calibration curve set using cyclodextrin extractions. Cyclodextrins recovered fumonisin better than PBS alone and about equivalent recoveries were obtained with hydroxypropyl β-cyclodextrin from Ashland Chemical Co. (HP β-CD-Ash), β-cyclodextrin from Wacker Chemical Co. (β-CD-Wack) and methyl-β-cyclodextrin from Sigma Chemical Co. β-cyclodextrin from Roquette Chemical Co. with 10% glycerol ethoxylate (β-CD . . . ProtG26) added to the diluent did not recover fumonisin as well as the other cyclodextrins without glycerol ethoxylate in the diluent.

Aqueous Based Extraction of Mycotoxin Reference Material Containing Multiple Concentrations of Mycotoxin While the non-foaming surfactants like NINEX® MT-630F, ECOSURF® EH-3 and TOXIMUL® had good recoveries of aflatoxin, fumonisin, zearalenone and ochratoxin, these surfactants are sold in large bulk quantities. NINEX® is a special order product from Stepan Chemical Co. where it is sold in orders of 7500 pounds or greater and distributors did not carry the product. ECOSURF® EH-3 is made by Dow Chemical Co. and distributed by Univar USA where the product is sold in a 435 pound drum at $2.25/lb. Finally, TOXIMUL® is also a special order surfactant made by Stepan Chemical. Each of these is also supplied as a liquid and a dry powder that could be added directly to grain for extraction was the preferred material. Since the surfactants were liquids and given their supply challenges, standard grade hydroxypropyl-cyclodextrin (trade name, CAVASOL®) made by Wacker Chemical Co. and distributed by Brentagg Solutions in 10 kg lots ($542 for 10 kg) was selected for further evaluation with REVEAL® Q+ lateral flow devices and VERATOX® ELISA.

Figure 5A:
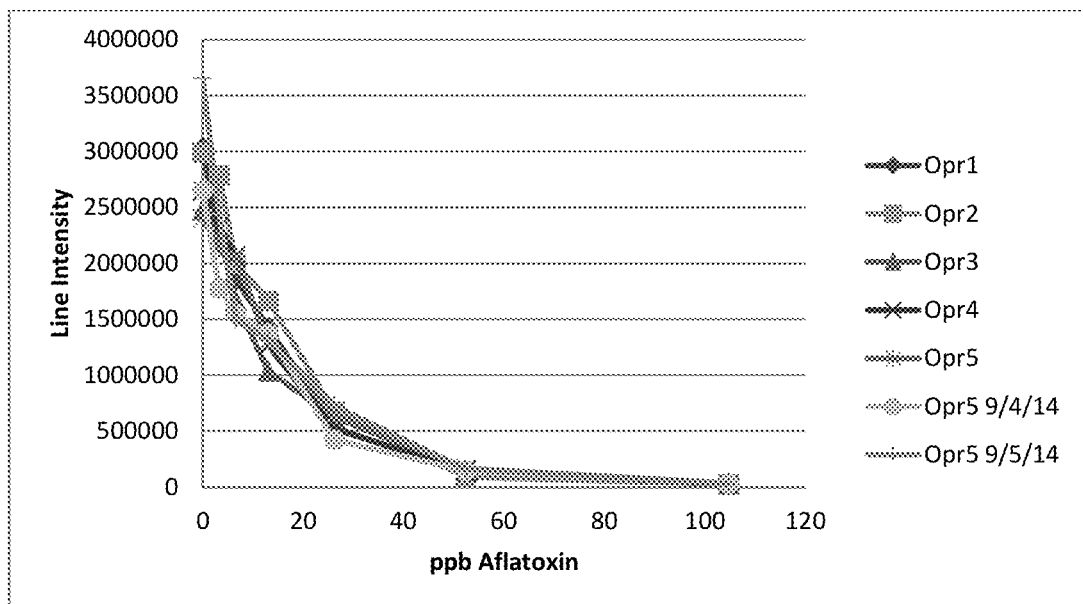
FIG. 5A is a graph showing REVEAL® Q+ for aflatoxin test line intensities for seven CAVASOL® extractions of ground corn reference material containing aflatoxin.
Figure 5B:
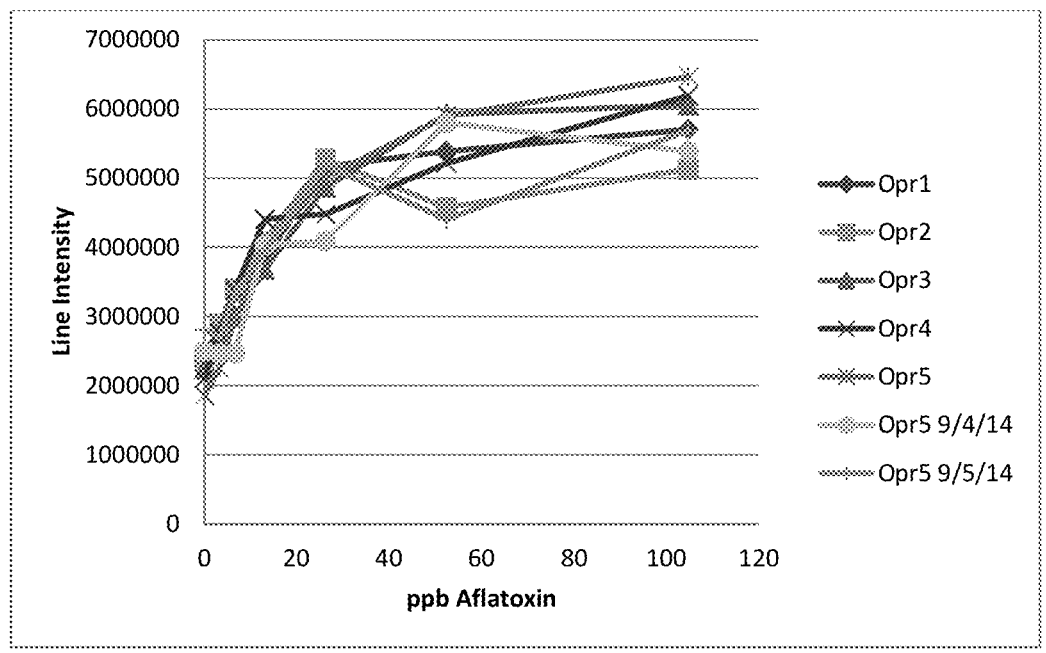
FIG. 5B is a graph showing Reveal® Q+ for aflatoxin control line intensities.
Figure 5C:
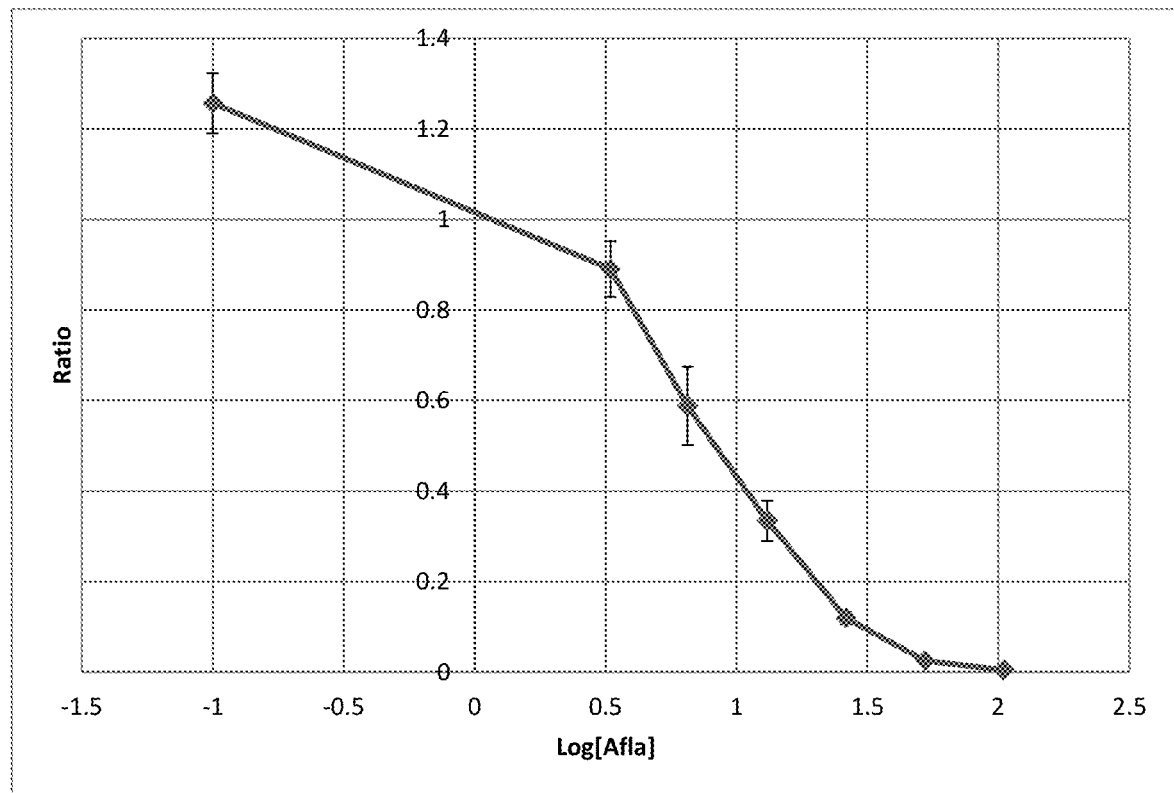
FIG. 5C is a graph showing REVEAL® Q+ for aflatoxin mean ratio of test to control line intensities for ground corn reference material.

Shown in FIGS. 5A-C are REVEAL® Q+ for Aflatoxin test and control line intensities and ratios of test to control line for seven different extractions of ground corn reference material containing 104.7, 52.4, 26.2, 13.1, 6.6, 3.3 ppb and non-detect aflatoxin. The 52.4 ppb dilution was prepared by 50:50 mixing the 104.7 ppb reference material with non-detect ground corn. The other serial dilutions were prepared mixing the diluted grain 50:50 with non-detect ground. Four different operators prepared grain samples using this procedure and extracted the samples using 2.6 g of CAVASOL®/PBS, pH 8.0 with 10 g of sample and 50.0 mL of Type 1 water. The solution was shaken for 3 min, filtered through a syringe filter, and then 0.6 mL of filtered extract was diluted into 0.6 mL of kit diluent. One of the operators did extractions on three different days. Test line intensity decreased and control line intensity increased with increasing aflatoxin concentration as expected (FIGS. 5A and 5B). The mean ratio of test to control line is shown in FIG. 5C along with one-standard deviation error bars. The precision of the results was good and quantitated amounts of aflatoxin were within the Grain Inspection, Packers & Stockyards Administration (GIPSA) acceptable ranges (Table 4) for all the data sets even when the curve sets for the data from the extremes were used to analyze the other data.

TABLE 4

REVEAL® Q+ for Aflatoxin Results for Cavasol®/PBS, pH 8.0 Extractions of Ground Corn Reference Material

| Expected ppb | Mean Observed ppb | SD | CV | % Passing GIPSA |
|---|---|---|---|---|
| ND | 1.9 | 0.50 | 26% | 100% |
| 3.3 | 3.8 | 0.46 | 12% | 100% |
| 6.6 | 6.4 | 0.74 | 11% | 100% |
| 13.1 | 12.0 | 1.59 | 13% | 100% |
| 26.2 | 25.2 | 2.00 | 8% | 100% |
| 52.4 | 56.7 | 4.04 | 7% | 98% |
| 104.7 | 102.5 | 14.82 | 14% | 100% |

Figure 6A:
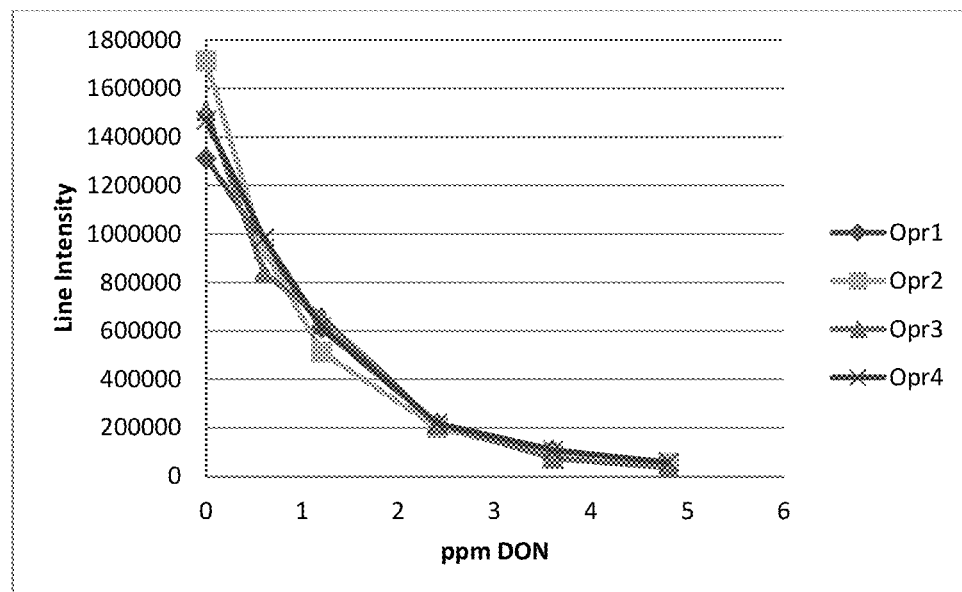
FIG. 6A is a graph showing REVEAL® Q+ for DON test line intensities for seven CAVASOL® extractions of ground wheat reference material containing don.
Figure 6B:
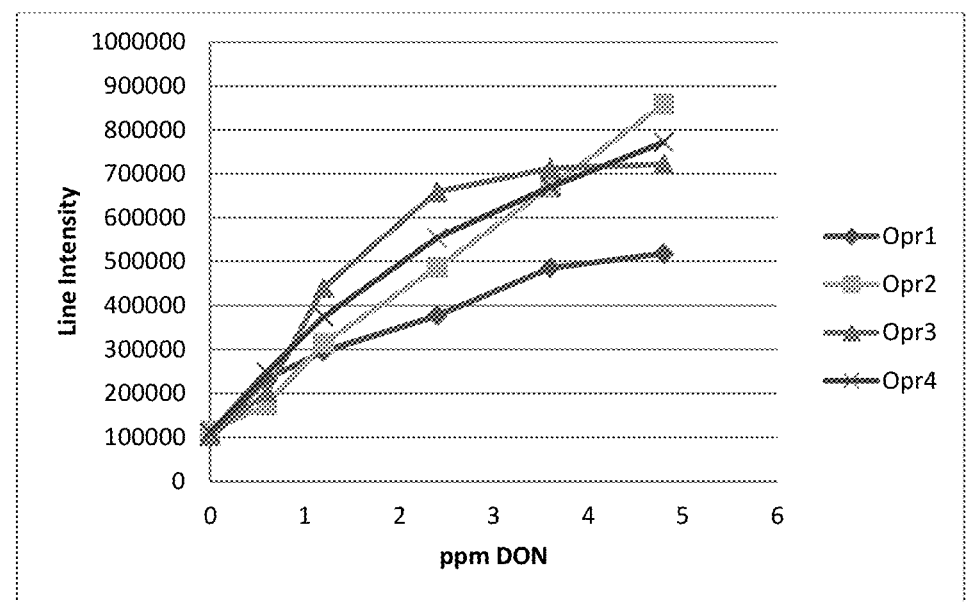
FIG. 6B is a graph showing REVEAL® Q+ for DON control line intensities.
Figure 6C:
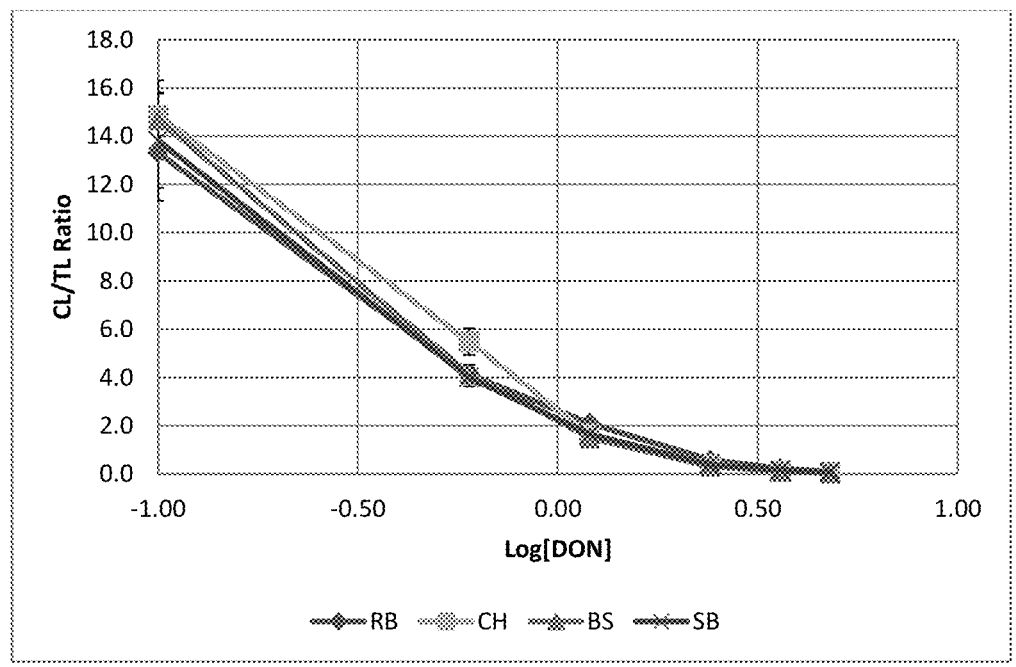
FIG. 6C is a graph showing REVEAL® Q+ for DON mean ratio of test to control line intensities for ground wheat reference material.

Shown in FIGS. 6A-C are REVEAL® Q+ for DON test and control line intensities and ratios of test to control line for seven different extractions of ground wheat reference material containing 4.8, 3.6, 2.4, 1.2, 0.6 ppm and non-detect DON. The 3.6 ppm dilution was prepared by 75:25 mixing the 4.8 ppm reference material with non-detect ground wheat. The other serial dilutions were prepared by 50:50 mixing the 4.8 ppm reference material with non-detect ground. Four different operators prepared grain samples using this procedure and extracted the samples using 2.6 g of CAVASOL®/PBS, pH 8.0 with 10 g of sample and 50.0 mL of Type 1 water. The solution was shaken for 3 min, filtered through a syringe filter, and then 50 µL of filtered extract was diluted into 1.5 mL of kit diluent. Test line intensity decreased and control line intensity increased with increasing DON concentration as expected (FIGS. 6A and 6B). The ratio of test to control line is shown in FIG. 6C along with one-standard deviation error bars. The precision of the results was good and quantitated amounts of DON were within GIPSA acceptable ranges (Table 5) for all the data sets even when the curve sets for the data from the extremes were used to analyze the other data.

TABLE 5

REVEAL® Q+ for DON Results for Cavasol®/PBS, pH 8.0 Extractions of Ground Wheat Reference Material

| Expected ppm | Mean Observed ppm | SD | CV | % Passing GIPSA |
|---|---|---|---|---|
| ND | 0.1 | 0.03 | 29% | 100% |
| 0.6 | 0.6 | 0.06 | 11% | 100% |
| 1.2 | 1.2 | 0.09 | 7% | 100% |
| 2.4 | 2.4 | 0.09 | 4% | 100% |
| 3.6 | 3.7 | 0.13 | 4% | 100% |
| 4.8 | 4.7 | 0.14 | 3% | 100% |

Figure 7:
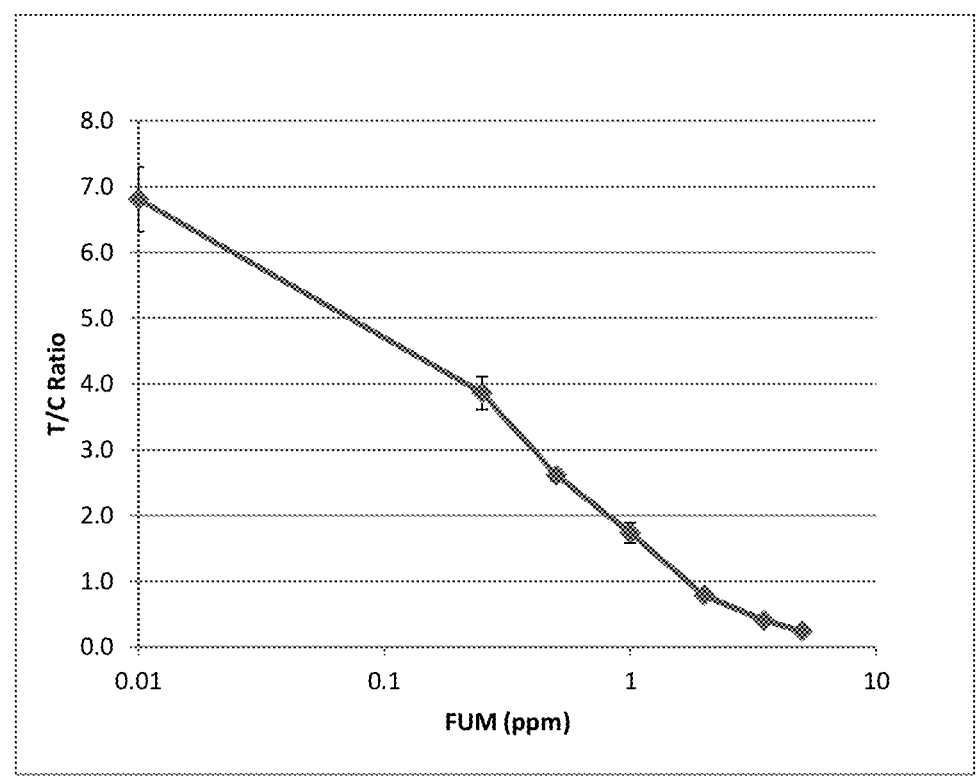
FIG. 7 is a graph showing REVEAL® Q+ for fumonisin mean ratio of test to control line intensities for ground corn reference material tested using the AccuScan Gold Reader.
Figure 8:
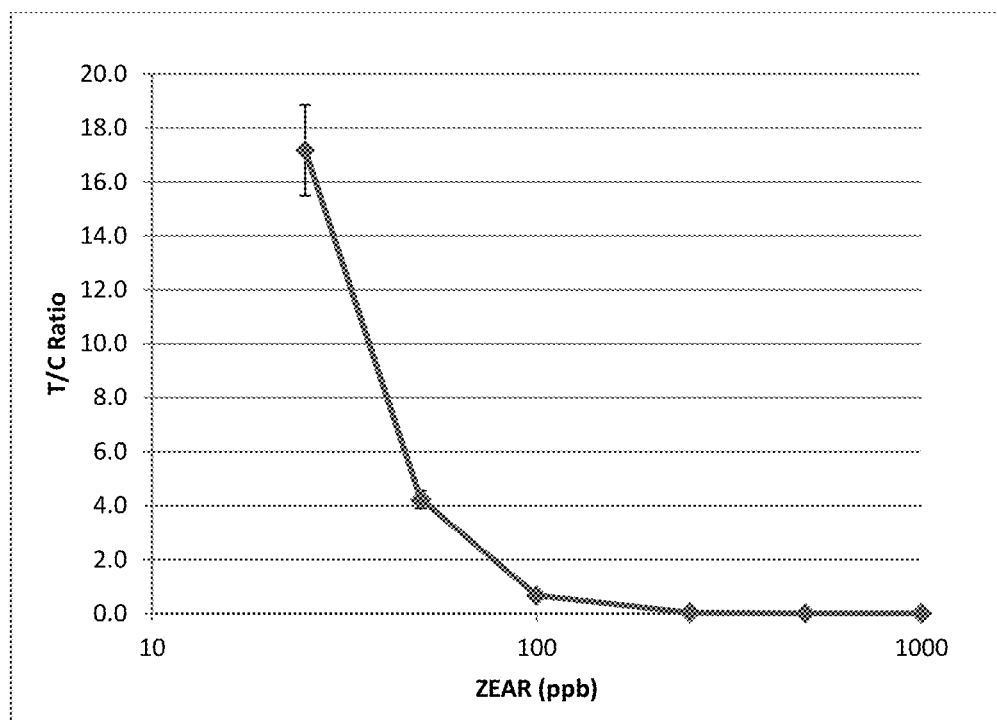
FIG. 8 is a graph showing REVEAL® Q+ for zearalenone mean ratio of test to control line intensities for ground corn reference material tested using the AccuScan Gold Reader.
Figure 9:
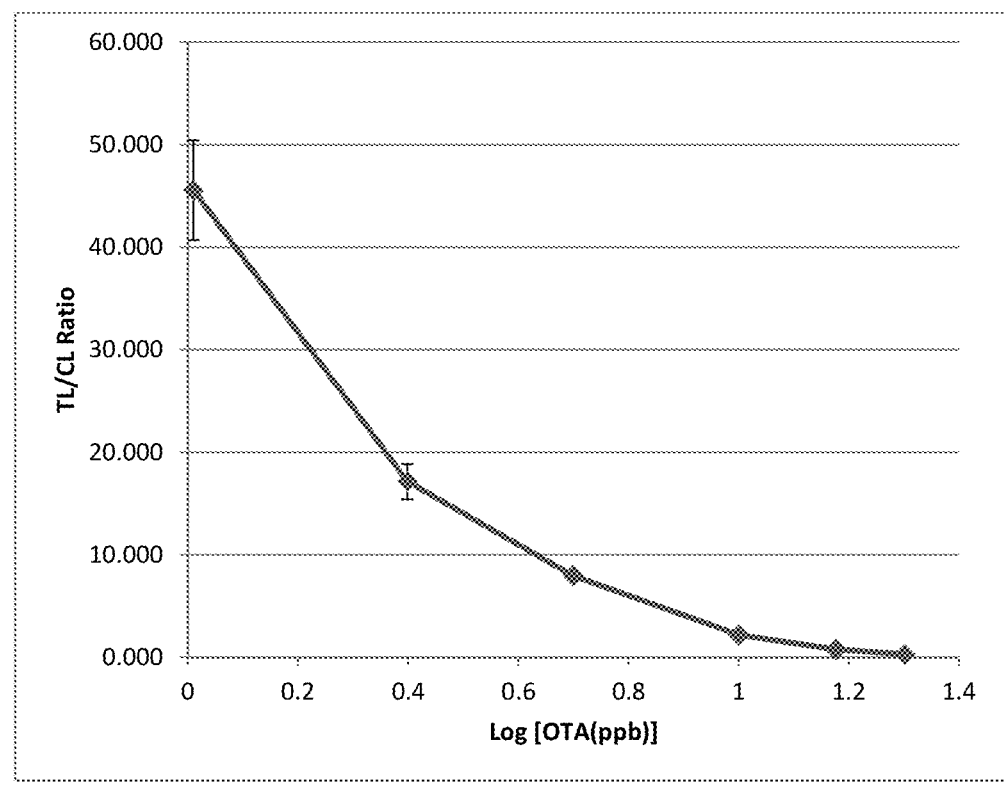
FIG. 9 is a graph showing REVEAL® Q+ for ochratoxin mean ratio of test to control line intensities for ground corn reference material tested using the AccuScan Gold Reader.

Calibration curve-sets were also established for Fumonisin, Zearalenone and Ochratoxin using CAVASOL®/PBS, pH 8.0 as the extractant for ground corn reference materials. Calibration curve sets for CAVASOL® extractions of these mycotoxins are shown in FIGS. 7, 8, and 9, respectively. For each of these extractions, 2.6 g of CAVASOL®/PBS, pH 8.0 was added to 10 g of ground corn and then 50 mL of Type 1 water was added. The solution was shaken for 3 min, filtered through a syringe filter, and then the filtered extract added to kit diluent. The dilution was dependent on the mycotoxin. REVEAL® Q+ devices were placed in 100 µL of the diluted extract, developed and the data acquired on AccuScan Gold readers.

A summary of results for CAVASOL® extractions of mycotoxins using the AccuScan Gold reader is provided in Table 6A. The last 2 columns in Table 6A compare the overall dilution of the current REVEAL® Q+ extraction methods and the CAVASOL® extraction. The total dilution for aflatoxin and ochratoxin extractions with CAVASOL® were the same at 1:10, but less dilution was necessary compared to the current solvent extractions. Total dilution for fumonisin, zearalenone were similar at 1:40 and 1:35, but greater dilution was required than for the solvent extractions. Dilution for DON was significantly greater than the other toxins for both the CAVASOL® and current water extractions.

Table 6B provides a summary of the average test and control line intensities for non-detect samples and samples containing mycotoxin at the high end of the calibration range. The last column of the table provides the dynamic range of the CAVASOL® extractions for each mycotoxin. Greater dynamic range provides greater resolution between samples at the high range of the calibration and non-detect samples; this can also be useful for discriminating intermediate levels of mycotoxin.

Tables 6A and 6B: Summary of Calibration Curve Set Results for CAVASOL® Extraction of Mycotoxins

TABLE 6A

| Toxin | Extraction Ratio | Extract Dilution Ratio | Quant Range | Current Total Dilution | Cavasol Total Dilution |
|---|---|---|---|---|---|
| DON -Wht | 1:5 | 1 + 30 | 0.3-6 ppm | 1:100 | 1:155 |
| OTA- Crn | 1:5 | 1 + 1 | 2-20 ppb | 1:12 | 1:10 |
| FUM- Crn | 1:5 | 1 + 7 | 0.3-6 ppm | 1:15 | 1:40 |
| ZEN- Crn | 1:5 | 1 + 6 | 50-1200 ppb | 1:15 | 1:35 |
| AFLA- Crn | 1:5 | 1 + 1 | 2.0-150 ppb | 1:25 | 1:10 |

TABLE 6B

| Toxin | Ctl Line Intensity (ND) | Ctl Line Intensity (High) | Test Line intensity (ND) | Test Line intensity (High) | T/C Ratio (ND) | T/C Ratio (High) | Dynamic Range |
|---|---|---|---|---|---|---|---|
| DON -Wht | 64566 | 941982 | 1453513 | 72798 | 22.9 | 0.0776 | 295 |
| OTA- Crn | 94978 | 902200 | 4312278 | 244595 | 45.6 | 0.275 | 166 |
| FUM- Crn | 320893 | 691052 | 1530294 | 367520 | 4.9 | 0.5 | 9.8 |
| ZEN- Crn | 2022465 | 4984108 | 3016964 | 48785 | 1.5 | 0.01 | 150 |
| AFLA- Crn | 2091039 | 3944618 | 1916442 | 2355.3 | 0.92 | 0.001* | ~92* |

Extraction of Specific Mycotoxins with Carbohydrates

Tables 7-19 provide the results of the extraction of the mycotoxins aflatoxin, zearalenone, fumonisin, and ochratoxin from ground corn with compositions comprising various extractants.

TABLE 7 provides the results of an experiment where 10 grams of ground corn containing aflatoxin (non-detect (control) & 18.7 ppb) was extracted with 30.0 mL of a composition containing 1% nanofibrillated cellulose (diluent = aflatoxin + 21.66% EtOH).

|  |  | 1 | 2 | Mean |
|---|---|---|---|---|
| ND | 1% Nanofibrillated Cellulose | 2.2 |  | 2.2 |
| 18.7 ppb | 1% Nanofibrillated Cellulose | 12.6 | 12.6 | 12.6 |

TABLE 8 provides the results of an experiment where 10 grams of ground corn containing aflatoxin (non-detect (control) & 18.7 ppb) was extracted with 30.0 mL of a composition containing 1% nanofibrillated cellulose (diluent = aflatoxin only).

|  |  | 1 | 2 | Mean |
|---|---|---|---|---|
| ND | 1% Nanofibrillated Cellulose | 10.1 |  | 10.1 |
| 18.7 ppb | 1% Nanofibrillated Cellulose | 26.3 | 23.6 | 25.0 |

TABLE 9 provides the results of an experiment where 10 grams of ground corn containing zearalenone (194.9 ppb and <5.0 ppb) was extracted with 30.0 mL of a composition containing 1% nanofibrillated cellulose or 1% D-Sorbitol in MQ water.

|  |  | 1 | 2 | Mean |
|---|---|---|---|---|
| ND | 1% D-Sorbitol | <25 |  | 24.0 |
| 194.9 ppb | 1% D-Sorbitol | 71.4 | 65.1 | 68.3 |
| ND | 1% Nanofibrillated Cellulose | <25 |  | 24.0 |
| 194.9 ppb | 1% Nanofibrillated Cellulose | 81.9 | 78.9 | 80.4 |

TABLE 10 provides the results of an experiment where 10 grams of ground corn containing fumonisin (ND & 4.2 ppm) was extracted with 30.0 mL of a composition containing 1% nanofibrillated cellulose or 1% D-Sorbitol. Diluent included 32.5% ethanol.

|  |  | 1 | 2 | Mean |
|---|---|---|---|---|
| ND | 1% D-Sorbitol | 0 |  | 0 |
| 4.2 ppb | 1% D-Sorbitol | 6.6 | 6.1 | 6.4 |
| ND | 1% Nanofibrillated Cellulose | 0 |  | 0 |
| 4.2 ppb | 1% Nanofibrillated Cellulose | 2.9 | 2.7 | 2.8 |

TABLE 11 provides the results of an experiment where 10 grams of ground corn containing ochratoxin (ND & 43.7 ppb) was extracted with 30.0 mL of a composition containing 1% nanofibrillated cellulose, 1% D-Sorbitol, or buffer alone. Diluent included 38.5% methanol.

| | | 1 | 2 | Mean |
|---|---|---|---|---|
| ND | 1% D-Sorbitol | 1.7 | | 1.7 |
| 43.7 ppb | 1% D-Sorbitol | 9.5 | 10.3 | 9.9 |
| ND | 1% Nanofibrillated Cellulose | 0 | | 1.0 |
| 43.7 ppb | 1% Nanofibrillated Cellulose | 2.3 | 1.8 | 2.1 |
| ND | 40 mM carbonate/bicarbonate buffer | 1.3 | | 1.3 |
| 43.7 ppb | 40 mM carbonate/bicarbonate buffer | 10.1 | 9.4 | 9.8 |

TABLE 12

Provides the results for 10 grams of ground corn containing 21 ppb aflatoxin extracted with 30.0 mL of 1% 2-hydroxyethyl cellulose.

| | | 1 | 2 | Mean |
|---|---|---|---|---|
| ND | 1% 2-hydroxyethyl Cellulose | 0 | | 0 |
| 21.0 ppb | 1% 2-hydroxyethyl Cellulose | 5.7 | 4.6 | 5.2 |

TABLE 13

Provides the results for 10 grams of ground corn containing 21 ppb aflatoxin extracted with 30 mL of 1% D-Sorbitol.

| | | 1 | 2 | Mean |
|---|---|---|---|---|
| ND | 1% D-Sorbitol | 0 | | 0 |
| 18.7 ppb | 1% D-Sorbitol | 6.9 | 6.8 | 6.9 |

TABLE 14 provides the results of an experiment where 10 grams of ground corn containing aflotoxin (ND & 17.8 ppb) was extracted with 30.0 mL of a composition containing 3% Neosorb-D-Sorbitol in MQ water only (200 μL filtrate in 400 μL Aflatoxin diluent).

| | | Mean | SD |
|---|---|---|---|
| ND | 3% Neosorb-D-Sorbitol | 11.2 | 0.4 |
| 21.0 ppb | 3% Neosorb-D-Sorbitol | 19.3 | 1.1 |

TABLE 15 provides the results of an experiment where 10 grams of ground corn containing aflotoxin (7 levels) was extracted with 30.0 mL of a composition containing 3% Neosorb-D-Sorbitol in MQ water with 10% Phoenoxol G-26 (600 μL filtrate in 1200 μL Aflatoxin diluent).

| | N = 10 | Mean | SD |
|---|---|---|---|
| ND | 3% Neosorb-D-Sorbitol in MQ water with 3.33, final % Phoenoxol G-26 | 3.9 | 0.5 |
| 2.65 | 3% Neosorb-D-Sorbitol in MQ water with 3.33, final % Phoenoxol G-26 | 4.4 | 0.6 |
| 5.3 | 3% Neosorb-D-Sorbitol in MQ water with 3.33, final % Phoenoxol G-26 | 5.3 | 0.7 |
| 10.6 | 3% Neosorb-D-Sorbitol in MQ water with 3.33, final % Phoenoxol G-26 | 6.9 | 0.6 |
| 17.8 | 3% Neosorb-D-Sorbitol in MQ water with 3.33, final % Phoenoxol G-26 | 10.2 | 0.4 |
| 54.85 | 3% Neosorb-D-Sorbitol in MQ water with 3.33, final % Phoenoxol G-26 | 27.1 | 1.3 |
| 109.7 | 3% Neosorb-D-Sorbitol in MQ water with 3.33, final % Phoenoxol G-26 | 62.7 | 2.8 |

TABLE 16 provides the results of an experiment where 10 grams of ground corn containing aflatoxin (ND & 18.7 ppb) was extracted with 30.0 mL of a composition containing 1% D-sorbitol - 200 μL filtrate in 200 μL diluent.

| | | 1 | 2 | Mean |
|---|---|---|---|---|
| ND | 1% D-sorbitol | 8.2 | | 8.2 |
| 18.7 ppb | 1% D-sorbitol | 21.2 | 20.9 | 21.1 |

TABLE 17 provides the results of an experiment where 10 grams of ground corn containing aflatoxin (ND, 17.8 and 109.7 ppb) was extracted with 30.0 mL of a composition containing 3% NEOSORB ®-D-Sorbitol with 10% PROTACHEM ™ G-26 (200 μL filtrate in 200 μL aflatoxin diluent).

| | | 1 | 2 | Mean | SD |
|---|---|---|---|---|---|
| ND | 3% NEOSORB ®-D-Sorbitol (Roquette) | 0.0 | 0.0 | 0.1 | 0.0 |
| 17.8 ppb | 3% NEOSORB ®-D-Sorbitol (Roquette) | 5.6 | 5.7 | 5.7 | 0.1 |
| 109.7 ppb | 3% NEOSORB ®-D-Sorbitol (Roquette) | 39.1 | 35.4 | 37.3 | 2.6 |

TABLE 18 provides the results of an experiment where 10 grams of ground corn containing aflatoxin (ND, 17.8 and 109.7 ppb) was extracted with 30.0 mL of a composition containing 3% NEOSORB ®-D-Sorbitol with 10% PROTACHEM ™G-26 (200 μL filtrate in 400 μL aflatoxin diluent).

|  |  | 1 | 2 | Mean | SD |
|---|---|---|---|---|---|
| ND | 3% NEOSORB ®-D-Sorbitol (Roquette) | 1.4 | 1.1 | 1.3 | 0.2 |
| 17.8 ppb | 3% NEOSORB ®-D-Sorbitol (Roquette) | 12.7 | 14.5 | 13.6 | 1.3 |
| 109.7 ppb | 3% NEOSORB ®-D-Sorbitol (Roquette) | 59.2 | 55.8 | 57.5 | 2.4 |

TABLE 19 provides the results of an experiment where 10 grams of ground corn containing zeorelenone (ND and 194.9 ppb) was extracted with 30.0 mL of a composition containing 1%-D-Sorbitol (100 μL filtrate in 300 μL or 600 μL diluent).

|  |  | 1 | 2 | Mean | 100 μL filtrate in 600 μL diluent |
|---|---|---|---|---|---|
| ND | 1% D-Sorbitol in 100 mM PBS, pH 8.0 | <25 |  | 24.0 | 100 μL filtrate in 600 μL diluent |
| 194.9 ppb | 1% D-Sorbitol in 100 mM PBS, pH 8.0 | 90.1 | 87.6 | 88.9 |  |
| ND | 1% D-Sorbitol in 100 mM PBS, pH 8.0 | 38.5 |  | 38.5 | 100 μL filtrate in 300 μL diluent |
| 194.9 ppb | 1% D-Sorbitol in 100 mM PBS, pH 8.0 | 176.8 | 165.9 | 171.4 |  |

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A method of extracting one or more mycotoxins from a foodstuff, comprising: contacting said foodstuff with a fully aqueous composition comprising 8 g/L of sodium chloride (NaCl), 13.8 g/L of disodium phosphate ($Na_2HPO_4$), 0.51 g/L of sodium dihydrogen phosphate ($NaH_2PO_4$), and 30 g/L of a hydroxypropyl-beta-cyclodextrin.

2. The method according to claim 1, wherein the foodstuff is a grain.

3. The method according to claim 2, wherein the grain is selected from the group consisting of barley, corn, fonio, kamut, millet, oats, popcorn, rice, rye, sorghum, spelt, teff, triticale, wheat, dry distiller grain, and corn gluten meal.

4. The method according to claim 3, wherein the grain is selected from the group consisting of corn, barley, wheat, and rice.

5. The method according to claim 1, wherein the one of more mycotoxins is selected from the group consisting of fumonisin, aflatoxin, zearalenone, ochratoxin, deoxynivalenol, and T2 toxin.

6. The method according to claim 1, wherein the method comprises the steps of:
   a) contacting the foodstuff matrix with the composition;
   b) optionally, removing the composition from the foodstuff; and
   c) contacting a lateral flow detection apparatus comprising a test strip and mycotoxin detector with the composition from step b.

7. The method according to claim 1, wherein two or more mycotoxins are extracted from the foodstuff.

8. The method according to claim 7, wherein the two or more mycotoxins are simultaneously extracted from the foodstuff.

* * * * *